United States Patent
Mutter

(10) Patent No.: US 6,868,342 B2
(45) Date of Patent: Mar. 15, 2005

(54) METHOD AND DISPLAY FOR MULTIVARIATE CLASSIFICATION

(75) Inventor: George L. Mutter, Chestnut Hill, MA (US)

(73) Assignee: The Brigham & Women's Hospital, Inc., Boston, MA (US)

( * ) Notice: Subject to any disclaimer, the term of this patent is extended or adjusted under 35 U.S.C. 154(b) by 221 days.

(21) Appl. No.: 09/977,054

(22) Filed: Oct. 12, 2001

(65) Prior Publication Data

US 2002/0143472 A1 Oct. 3, 2002

Related U.S. Application Data

(60) Provisional application No. 60/252,290, filed on Nov. 21, 2000, and provisional application No. 60/240,403, filed on Oct. 13, 2000.

(51) Int. Cl.$^7$ .............................. G06F 19/00; B06K 9/52
(52) U.S. Cl. .............................. 702/21; 706/20; 382/228
(58) Field of Search .............................. 702/21, 19, 27; 706/20; 382/228, 224

(56) References Cited

U.S. PATENT DOCUMENTS

| | | | |
|---|---|---|---|
| 5,739,808 A | | 4/1998 | Suga et al. |
| 5,871,697 A | * | 2/1999 | Rothberg et al. .......... 422/68.1 |
| 5,871,698 A | | 2/1999 | Laguna et al. |
| 6,214,556 B1 | | 4/2001 | Olek et al. |
| 6,647,341 B1 | * | 11/2003 | Golub et al. ................. 702/19 |

FOREIGN PATENT DOCUMENTS

| WO | WO 99/28498 A2 | 6/1999 |
|---|---|---|

OTHER PUBLICATIONS

Furey et al., "Support vector machine classification and validation of cancer tissue samples using microarray expression data", *Bioinformatics*, vol. 16, No. 10, pp. 906–914 (2000).
Golub et al., *Science* 286: 531–537 (1999).

* cited by examiner

*Primary Examiner*—Marjorie Moran
(74) *Attorney, Agent, or Firm*—Wolf, Greenfield & Sacks, P.C.

(57) ABSTRACT

The present invention represents a new approach to data analysis for multivariate classification, particularly as used in medical diagnostics. The invention is in part an intuitive decision making tool for rapid classification of "objects" (e.g., cell, tissue or tumor samples) from evaluation of many simultaneous "variables" (e.g., quantitative gene expression profiles). The data analysis methods of the invention provide the end user with a simplified and robust output for diagnostic classification of objects based on identifying and evaluating multiple variables of predetermined diagnostic relevance. The raw data generated by analysis of the variables is transformed by application or appropriate algorithms to scaleless rank differentials between the variables. The rank orders of variables are used to classify tissues based on readily observable user interfaces, such as a graphical (e.g., visual) user interface or an auditory user interface.

6 Claims, 35 Drawing Sheets

ALL TEST CASES

| | A | B | C | D | E | F | G | H | I | J | K | L |
|---|---|---|---|---|---|---|---|---|---|---|---|---|
| 1 | Probe | AllTMean | AMLTMean | AMLTDIFFN | AMLTDiff | AMLTFold | AMLTTST | AMLTTRK | ALLTRANK | AMLTRANK | DIFFTRANK | COLORTS |
| 2 | M13792_at | 6784.8 | 1743.36 | -5041.45 | 5041.45 | 3.89 | 0.00001 | 55.00 | 100.00 | 77.00 | 1.00 | blue |
| 3 | L06797_s_at | 6381.67 | 1960.73 | -4420.94 | 4420.94 | 3.25 | 0.00020 | 121.00 | 99.00 | 81.00 | 2.00 | blue |
| 4 | M92287_at | 3829.30 | 274.00 | -3555.30 | 3555.30 | 13.98 | 0.000001 | 26.00 | 94.00 | 37.00 | 3.00 | blue |
| 5 | U05259_rna1_at | 3467.26 | 20.00 | -3447.26 | 3447.26 | 173.35 | 0.000001 | 43.00 | 93.00 | 4.00 | 4.00 | blue |
| 6 | X59417_at | 4361.37 | 1138.18 | -3223.19 | 3223.19 | 3.83 | 0.00001 | 46.00 | 98.00 | 65.00 | 5.00 | blue |
| 7 | U22376_cds2_s_at | 3863.30 | 673.73 | -3189.57 | 3189.57 | 5.73 | 0.000000 | 19.00 | 95.00 | 55.00 | 6.00 | blue |
| 8 | M11722_at | 3022.07 | 134.91 | -2887.16 | 2887.16 | 22.40 | 0.000000 | 16.00 | 92.00 | 25.00 | 7.00 | blue |
| 9 | Z15115_at | 4213.00 | 1365.27 | -2847.73 | 2847.73 | 3.09 | 0.000007 | 45.00 | 97.00 | 72.00 | 8.00 | blue |
| 10 | X03934_at | 2878.67 | 55.45 | -2823.21 | 2823.21 | 51.91 | 0.000001 | 23.00 | 91.00 | 16.00 | 9.00 | blue |
| 11 | HG1612-H1612_at | 3871.67 | 1156.84 | -2715.03 | 2715.03 | 3.35 | 0.000001 | 48.00 | 96.00 | 66.00 | 10.00 | blue |
| 12 | X97267_rna1_s_at | 2389.63 | 386.36 | -2003.27 | 2003.27 | 6.18 | 0.000003 | 49.00 | 90.00 | 45.00 | 11.00 | blue |
| 13 | Z69881_at | 2197.52 | 281.09 | -1916.43 | 1916.43 | 7.82 | 0.000001 | 68.00 | 88.00 | 39.00 | 12.00 | blue |
| 14 | M29696_at | 2218.67 | 319.73 | -1898.94 | 1898.94 | 6.94 | 0.000001 | 47.00 | 89.00 | 42.00 | 13.00 | blue |
| 15 | M12959_s_at | 1844.48 | 241.45 | -1603.03 | 1603.03 | 7.64 | 0.000004 | 71.00 | 86.00 | 34.00 | 14.00 | blue |
| 16 | J04615_at | 2020.89 | 439.73 | -1581.16 | 1581.16 | 4.60 | 0.000000 | 18.00 | 87.00 | 49.00 | 15.00 | blue |
| 17 | U32944_at | 1701.56 | 292.73 | -1411.83 | 1411.83 | 5.82 | 0.000021 | 124.00 | 85.00 | 40.00 | 16.00 | blue |
| 18 | X74262_at | 1411.19 | 253.00 | -1158.19 | 1158.19 | 5.58 | 0.000003 | 67.00 | 83.00 | 36.00 | 17.00 | blue |
| 19 | L47738_at | 1230.15 | 80.27 | -1149.88 | 1149.88 | 15.32 | 0.000001 | 13.00 | 79.00 | 18.00 | 18.00 | blue |
| 20 | X62535_at | 1105.85 | 20.00 | -1085.85 | 1085.85 | 55.29 | 0.000001 | 17.00 | 77.00 | 1.00 | 19.00 | blue |
| 21 | M31523_at | 1310.59 | 238.91 | -1071.68 | 1071.68 | 5.49 | 0.000001 | 56.00 | 81.00 | 33.00 | 20.00 | blue |
| 22 | D86983_at | 1077.89 | 20.00 | -1057.89 | 1057.89 | 53.89 | 0.000000 | 44.00 | 76.00 | 5.00 | 21.00 | blue |
| 23 | L05148_at | 1055.96 | 20.00 | -1035.96 | 1035.96 | 52.80 | 0.000020 | 118.00 | 74.00 | 7.00 | 22.00 | blue |
| 24 | D26156_s_at | 1306.00 | 379.36 | -926.64 | 926.64 | 3.44 | 0.000095 | 30.00 | 80.00 | 43.00 | 23.00 | blue |
| 25 | U29175_at | 1202.67 | 382.55 | -820.12 | 820.12 | 3.14 | 0.000001 | 79.00 | 78.00 | 44.00 | 24.00 | blue |
| 26 | U90552_s_at | 917.37 | 133.64 | -783.73 | 783.73 | 6.86 | 0.000000 | 15.00 | 70.00 | 24.00 | 25.00 | blue |
| 27 | J05243_at | 860.63 | 125.55 | -735.08 | 735.08 | 6.86 | 0.000020 | 115.00 | 68.00 | 22.00 | 26.00 | blue |
| 28 | U97105_at | 1009.22 | 276.45 | -732.77 | 732.77 | 3.65 | 0.0009 | 96.00 | 73.00 | 38.00 | 27.00 | blue |
| 29 | M91437_at | 895.96 | 171.45 | -724.51 | 724.51 | 5.23 | 0.00015 | 64.00 | 69.00 | 27.00 | 28.00 | blue |
| 30 | X76648_at | 930.37 | 245.73 | -684.64 | 684.64 | 3.79 | 0.000013 | 106.00 | 71.00 | 35.00 | 29.00 | blue |
| 31 | D14658_at | 981.70 | 315.00 | -666.70 | 666.70 | 3.12 | 0.000004 | 90.00 | 58.00 | 19.00 | 30.00 | blue |
| 32 | M63838_s_at | 785.44 | 230.36 | -556.08 | 556.08 | 3.14 | 0.000013 | 89.00 | 72.00 | 41.00 | 31.00 | blue |
| 33 | U31814_at | 669.52 | 149.09 | -520.43 | 520.43 | 4.49 | 0.00011 | 105.00 | 67.00 | 32.00 | 32.00 | blue |
| 34 | M31211_s_at | 538.15 | 45.45 | -492.69 | 492.69 | 11.84 | 0.000000 | 100.00 | 65.00 | 28.00 | 33.00 | blue |
| 35 | L00058_at | 498.22 | 23.64 | -474.59 | 474.59 | 21.08 | 0.000017 | 5.00 | 62.00 | 15.00 | 34.00 | blue |
| 36 | U79274_at | 625.07 | 165.55 | -459.53 | 459.53 | 3.78 | 0.000009 | 115.00 | 59.00 | 9.00 | 35.00 | blue |
| 37 | M22898_at | 607.30 | 148.91 | -458.39 | 458.39 | 4.08 | 0.000003 | 96.00 | 64.00 | 29.00 | 36.00 | blue |
| 38 | X68560_at | 518.74 | 145.82 | -372.92 | 372.92 | 3.56 | 0.000013 | 64.00 | 63.00 | 27.00 | 36.00 | blue |
| 39 | L07758_at | 456.07 | 85.82 | -370.26 | 370.26 | 5.31 | 0.000006 | 106.00 | 61.00 | 26.00 | 37.00 | blue |
| 40 | L42572_at | 428.00 | 89.64 | -338.36 | 338.36 | 4.77 | 0.000006 | 90.00 | 58.00 | 19.00 | 38.00 | blue |
| 41 | L41870_at | 357.15 | 25.64 | -331.51 | 331.51 | 13.93 | 0.000000 | 34.00 | 56.00 | 20.00 | 39.00 | blue |
| 42 | U25435_at | 419.00 | 102.18 | -316.82 | 316.82 | 4.10 | 0.000000 | 85.00 | 51.00 | 10.00 | 40.00 | blue |
| 43 | Y08612_at | 359.30 | 44.73 | -314.57 | 314.57 | 8.03 | 0.000001 | 47.00 | 55.00 | 21.00 | 41.00 | blue |
| 44 | D83783_at | 347.89 | 43.27 | -304.62 | 304.62 | 8.04 | 0.000023 | 125.00 | 52.00 | 14.00 | 42.00 | blue |
| 45 | D43945_at | 369.37 | 65.18 | -304.19 | 304.19 | 5.67 | 0.000006 | 83.00 | 53.00 | 17.00 | 43.00 | blue |

| | A | B | C | D | E | F | G | H | I | J | K | L |
|---|---|---|---|---|---|---|---|---|---|---|---|---|
| 1 | Probe | ALLTMean | AVLTMean | ALMTDIFPN | ALMTDiff | ALMTFold | ALMTTST | ALMTTRK | ALLTRANK | AMLTRANK | DIFFTRANK | COLORT$ |
| 46 | S50223_at | 323.26 | 39.73 | -283.53 | 283.53 | 8.14 | 0.00020 | 122.00 | 47.00 | 11.00 | 45.00 | blue |
| 67 | U79285_at | 283.11 | 20.00 | -263.11 | 263.11 | 14.16 | 0.00009 | 95.00 | 43.00 | 6.00 | 46.00 | blue |
| 48 | D21262_at | 255.63 | 20.00 | -235.63 | 235.63 | 12.78 | 0.00020 | 35.00 | 42.00 | 3.00 | 47.00 | blue |
| 49 | U19844_at | 201.56 | 20.00 | -181.56 | 181.56 | 10.08 | 0.00023 | 126.00 | 41.00 | 8.00 | 48.00 | blue |
| 50 | M77142_at | 200.11 | 20.00 | -180.11 | 180.11 | 10.01 | 0.00004 | 29.00 | 39.00 | 2.00 | 49.00 | blue |
| 51 | U28833_at | 160.26 | 44.00 | -116.26 | 116.26 | 3.64 | 0.00003 | 77.00 | 34.00 | 13.00 | 50.00 | blue |
| 52 | X17648_at | 28.37 | 133.18 | 104.81 | 104.81 | 4.69 | 0.00004 | 65.00 | 13.00 | 23.00 | 51.00 | red |
| 53 | D49950_at | 20.00 | 216.64 | 196.64 | 196.64 | 10.83 | 0.00003 | 4.00 | 1.00 | 31.00 | 52.00 | red |
| 54 | U73960_at | 88.19 | 447.09 | 358.91 | 358.91 | 5.07 | 0.00001 | 39.00 | 26.00 | 51.00 | 53.00 | red |
| 55 | S76638_at | 34.30 | 403.82 | 369.52 | 369.52 | 11.77 | 0.00005 | 80.00 | 14.00 | 47.00 | 54.00 | red |
| 56 | M80754_at | 43.96 | 420.36 | 376.40 | 376.40 | 9.56 | 0.00005 | 28.00 | 17.00 | 48.00 | 55.00 | red |
| 57 | M31166_at | 20.00 | 396.73 | 376.73 | 376.73 | 19.84 | 0.00000 | 12.00 | 3.00 | 46.00 | 56.00 | red |
| 58 | X16665_at | 91.48 | 480.91 | 389.43 | 389.43 | 5.26 | 0.00001 | 33.00 | 27.00 | 52.00 | 57.00 | red |
| 59 | U05572_s_at | 20.00 | 445.73 | 425.73 | 425.73 | 22.29 | 0.00000 | 40.00 | 7.00 | 50.00 | 58.00 | red |
| 60 | U41813_at | 129.19 | 589.82 | 440.63 | 440.63 | 4.41 | 0.00000 | 56.00 | 30.00 | 53.00 | 59.00 | red |
| 61 | X70297_at | 36.56 | 662.45 | 625.90 | 625.90 | 18.12 | 0.00001 | 3.00 | 16.00 | 54.00 | 60.00 | red |
| 62 | M54995_at | 35.15 | 675.36 | 640.22 | 640.22 | 19.21 | 0.00000 | 22.00 | 15.00 | 57.00 | 61.00 | red |
| 63 | M23197_at | 57.33 | 708.82 | 651.48 | 651.48 | 12.36 | 0.00001 | 20.00 | 20.00 | 58.00 | 62.00 | red |
| 64 | U61836_at | 20.00 | 674.82 | 654.82 | 654.82 | 33.74 | 0.00000 | 20.00 | 4.00 | 56.00 | 63.00 | red |
| 65 | D26579_at | 109.41 | 794.27 | 684.87 | 684.87 | 7.26 | 0.00004 | 76.00 | 28.00 | 61.00 | 64.00 | red |
| 66 | M83652_s_at | 20.00 | 766.36 | 746.36 | 746.36 | 38.32 | 0.00005 | 82.00 | 9.00 | 59.00 | 65.00 | red |
| 67 | U41767_s_at | 20.00 | 766.45 | 746.45 | 745.45 | 38.32 | 0.00005 | 81.00 | 8.00 | 60.00 | 66.00 | red |
| 68 | Y00339_at | 52.41 | 946.91 | 894.50 | 894.50 | 18.07 | 0.00006 | 73.00 | 19.00 | 62.00 | 67.00 | red |
| 69 | M33493_s_at | 20.00 | 948.45 | 928.45 | 928.45 | 47.42 | 0.00000 | 86.00 | 10.00 | 63.00 | 68.00 | red |
| 70 | HG2987-HT3127_s_at | 44.48 | 983.27 | 938.79 | 938.79 | 22.11 | 0.00001 | 24.00 | 18.00 | 64.00 | 69.00 | red |
| 71 | X07743_at | 150.15 | 1167.36 | 1017.22 | 1017.22 | 7.77 | 0.00001 | 51.00 | 32.00 | 67.60 | 70.00 | red |
| 72 | U46499_at | 182.48 | 1200.36 | 1017.88 | 1017.88 | 6.58 | 0.00001 | 10.00 | 37.00 | 69.00 | 71.00 | red |
| 73 | M83667_rna1_s_at | 66.59 | 1195.82 | 1129.23 | 1129.23 | 17.96 | 0.00004 | 74.00 | 22.00 | 66.00 | 72.00 | red |
| 74 | M81695_s_at | 370.00 | 1811.64 | 1441.64 | 1441.64 | 4.90 | 0.00002 | 66.00 | 36.00 | 73.00 | 73.00 | red |
| 75 | Y12670_at | 307.04 | 1439.64 | 1132.60 | 1132.60 | 4.69 | 0.00001 | 61.00 | 45.00 | 72.00 | 74.00 | red |
| 76 | J47379_at | 308.63 | 1842.73 | 1534.10 | 1534.10 | 5.97 | 0.00001 | 57.00 | 46.00 | 70.00 | 75.00 | red |
| 77 | M19508_xpl3_s_at | 20.00 | 1581.91 | 1551.91 | 1561.91 | 79.10 | 0.00006 | 25.00 | 29.00 | 76.00 | 76.00 | red |
| 78 | M33195_at | 128.00 | 1302.64 | 1282.64 | 1282.64 | 65.13 | 0.00006 | 88.00 | 11.00 | 74.00 | 77.00 | red |
| 79 | M16038_at | 201.41 | 1551.00 | 1349.59 | 1349.59 | 7.70 | 0.00001 | 41.00 | 40.00 | 74.00 | 78.00 | red |
| 80 | X85116_mal_s_at | 175.63 | 1577.00 | 1401.37 | 1401.37 | 8.98 | 0.00000 | 50.00 | 38.00 | 75.00 | 79.00 | red |
| 81 | M20203_s_at | 166.70 | 1911.27 | 1744.57 | 1744.57 | 11.47 | 0.00003 | 36.00 | 35.00 | 80.00 | 81.00 | red |
| 82 | M95678_at | 185.89 | 2155.45 | 1969.57 | 1969.57 | 11.60 | 0.00003 | 70.00 | 38.00 | 83.00 | 82.00 | red |
| 83 | U02020_at | 513.48 | 2531.55 | 2017.05 | 2018.06 | 4.93 | 0.00006 | 84.00 | 50.00 | 86.00 | 83.00 | red |
| 84 | U09209_s_at | 20.00 | 2042.36 | 2022.36 | 2022.35 | 102.12 | 0.00000 | 21.00 | 5.00 | 82.00 | 84.00 | red |
| 85 | M27783_s_at | 27.19 | 2271.09 | 2243.91 | 2243.91 | 86.54 | 0.00003 | 63.00 | 12.00 | 84.00 | 85.00 | red |
| 86 | M30703_s_at | 66.11 | 2520.36 | 2454.25 | 2454.25 | 38.12 | 0.00003 | 1.00 | 6.00 | 85.00 | 86.00 | red |
| 87 | D88422_at | 73.70 | 2588.36 | 2514.66 | 2514.66 | 35.12 | 0.00006 | 32.00 | 21.00 | 87.00 | 87.00 | red |
| 88 | M57731_s_at | 1066.56 | 3767.45 | 2700.90 | 2700.90 | 3.53 | 0.00000 | 31.00 | 75.00 | 90.00 | 88.00 | red |
| 89 | L08246_at | | | | | | | | | | | |

| | A | B | C | D | E | F | G | H | I | J | K | L |
|---|---|---|---|---|---|---|---|---|---|---|---|---|
| 1 | Probe | ALLTMean | AMLTMean | ALMTDIFPN | ALMTDiff | ALMTFold | ALMTTST | ALMTTRK | ALLTRANK | AMLTRANK | DIFFRANK | COLOR$ |
| 90 | X95735_at | 68.37 | 2779.91 | 2711.54 | 2711.54 | 40.66 | 0.00000 | 8.00 | 24.00 | 88.00 | 89.00 | red |
| 91 | M84526_at | 20.00 | 3505.91 | 3485.91 | 3485.91 | 175.30 | 0.00000 | 7.00 | 2.00 | 89.00 | 90.00 | red |
| 92 | X62320_at | 304.93 | 4047.55 | 3742.62 | 3742.62 | 13.27 | 0.00005 | 78.00 | 44.00 | 91.00 | 91.00 | red |
| 93 | M19507_at | 333.19 | 4855.55 | 4522.36 | 4522.36 | 14.57 | 0.00003 | 69.00 | 48.00 | 92.00 | 92.00 | red |
| 94 | M63138_at | 453.22 | 5144.27 | 4691.05 | 4691.05 | 11.35 | 0.00000 | 37.00 | 57.00 | 94.00 | 93.00 | red |
| 95 | J04990_at | 135.59 | 4919.73 | 4784.13 | 4784.13 | 36.28 | 0.00002 | 60.00 | 31.00 | 93.00 | 94.00 | red |
| 96 | X17042_at | 1642.81 | 7108.73 | 5465.91 | 5465.91 | 4.33 | 0.00001 | 52.00 | 84.00 | 98.00 | 95.00 | red |
| 97 | X14008_mol_f_at | 1398.74 | 6939.36 | 5540.62 | 5540.62 | 4.96 | 0.00006 | 87.00 | 82.00 | 97.00 | 96.00 | red |
| 98 | M28130_mal_s_at | 339.67 | 6304.82 | 5965.15 | 5965.15 | 18.56 | 0.00000 | 14.00 | 49.00 | 65.00 | 97.00 | red |
| 99 | M96326_mal_at | 67.26 | 6872.36 | 6805.10 | 6805.10 | 102.18 | 0.00000 | 11.00 | 23.00 | 96.00 | 98.00 | red |
| 100 | M27891_at | 159.41 | 7327.82 | 7168.41 | 7168.41 | 45.97 | 0.00000 | 6.00 | 33.00 | 99.00 | 99.00 | red |
| 101 | Y00787_s_at | 784.63 | 10479.09 | 9694.46 | 9694.46 | 13.36 | 0.00000 | 27.00 | 66.00 | 100.00 | 100.00 | red |

Fig. 7-3

| Gene | ALLITMean | AMLITMean | ALLTRANK | AMLTRANK | DIFFTRANK | COLOR$ | Symbol | ALL39GPT | ALL40GPT | ALL42GPT | ALL47GPT | ALL48GPT | ALL49GPT |
|---|---|---|---|---|---|---|---|---|---|---|---|---|---|
| x4268 | 20 | 217 | 1 | 31 | 52 | red | 1 | 20 | 234 | 20 | 20 | 20 | 20 |
| x3767 | 20 | 3506 | 2 | 89 | 90 | red | 1 | 20 | 20 | 20 | 20 | 20 | 20 |
| x5837 | 20 | 397 | 3 | 46 | 56 | red | 1 | 20 | 20 | 20 | 20 | 20 | 20 |
| x4620 | 20 | 675 | 4 | 56 | 63 | red | 1 | 20 | 20 | 20 | 20 | 20 | 20 |
| x1311 | 20 | 2042 | 5 | 62 | 84 | red | 1 | 20 | 20 | 1162 | 20 | 20 | 20 |
| x857 | 20 | 1582 | 6 | 76 | 80 | red | 1 | 20 | 20 | 315 | 20 | 20 | 20 |
| x1504 | 20 | 446 | 7 | 50 | 58 | red | 1 | 20 | 20 | 20 | 20 | 20 | 20 |
| x2862 | 20 | 766 | 8 | 60 | 66 | red | 1 | 20 | 20 | 20 | 806 | 20 | 20 |
| x1662 | 20 | 766 | 9 | 59 | 65 | red | 1 | 20 | 20 | 20 | 20 | 20 | 20 |
| x4122 | 20 | 948 | 10 | 63 | 68 | red | 1 | 20 | 20 | 20 | 20 | 20 | 20 |
| x984 | 20 | 1303 | 11 | 71 | 75 | red | 1 | 20 | 20 | 20 | 20 | 20 | 20 |
| x6853 | 27 | 2271 | 12 | 84 | 85 | red | 1 | 20 | 20 | 20 | 67 | 20 | 20 |
| x5266 | 28 | 133 | 13 | 23 | 51 | red | 1 | 20 | 20 | 20 | 20 | 20 | 20 |
| x2876 | 34 | 404 | 14 | 47 | 54 | red | 1 | 20 | 20 | 20 | 20 | 20 | 20 |
| x350 | 35 | 675 | 151 | 57 | 61 | red | 1 | 20 | 20 | 20 | 20 | 20 | 20 |
| x6583 | 37 | 662 | 16 | 54 | 60 | red | 1 | 20 | 373 | 20 | 20 | 20 | 20 |
| x880 | 44 | 420 | 17 | 46 | 55 | red | 1 | 20 | 20 | 20 | 20 | 60 | 20 |
| x2234 | 44 | 983 | 18 | 64 | 69 | red | 1 | 20 | 20 | 20 | 20 | 20 | 20 |
| x1319 | 52 | 947 | 19 | 62 | 67 | red | 1 | 20 | 20 | 2113 | 470 | 263 | 20 |
| x2330 | 57 | 709 | 20 | 58 | 62 | red | 1 | 20 | 244 | 20 | 20 | 20 | 20 |
| x5263 | 66 | 2520 | 21 | 85 | 86 | red | 1 | 20 | 20 | 189 | 20 | 20 | 20 |
| x3221 | 67 | 1196 | 22 | 68 | 72 | red | 1 | 20 | 20 | 20 | 20 | 20 | 20 |
| x2835 | 67 | 6872 | 23 | 96 | 98 | red | 1 | 20 | 20 | 20 | 20 | 20 | 20 |
| x6275 | 68 | 2780 | 24 | 88 | 69 | red | 1 | 20 | 20 | 20 | 20 | 20 | 20 |
| x6019 | 74 | 2588 | 25 | 87 | 87 | red | 1 | 20 | 20 | 20 | 20 | 20 | 20 |
| x4287 | 88 | 447 | 26 | 51 | 53 | red | 1 | 20 | 20 | 486 | 20 | 116 | 20 |
| x4230 | 91 | 481 | 27 | 52 | 57 | red | 1 | 20 | 443 | 110 | 20 | 20 | 964 |
| x5827 | 109 | 794 | 28 | 61 | 64 | red | 1 | 20 | 20 | 233 | 20 | 20 | 20 |
| x2970 | 128 | 1294 | 29 | 70 | 74 | red | 1 | 20 | 20 | 20 | 342 | 20 | 20 |
| x6775 | 129 | 570 | 30 | 53 | 59 | red | 1 | 20 | 20 | 20 | 20 | 20 | 20 |
| x3228 | 136 | 4920 | 31 | 93 | 94 | red | 1 | 20 | 20 | 550 | 20 | 20 | 20 |
| x5691 | 150 | 1167 | 32 | 67 | 70 | red | 1 | 20 | 20 | 258 | 575 | 542 | 20 |
| x7113 | 159 | 7328 | 33 | 99 | 99 | red | 1 | 20 | 20 | 20 | 20 | 20 | 20 |
| x4488 | 160 | 44 | 34 | 13 | 50 | blue | 2 | 236 | 92 | 312 | 20 | 1078 | 72 |
| x3194 | 167 | 1911 | 35 | 80 | 81 | red | 1 | 20 | 20 | 20 | 20 | 20 | 20 |
| x3532 | 176 | 1577 | 36 | 75 | 77 | red | 1 | 20 | 20 | 20 | 20 | 20 | 20 |
| x5593 | 182 | 1200 | 37 | 69 | 71 | red | 1 | 20 | 20 | 20 | 20 | 20 | 20 |
| x862 | 186 | 2155 | 38 | 83 | 82 | red | 1 | 20 | 20 | 425 | 187 | 227 | 75 |
| x855 | 200 | 20 | 39 | 2 | 49 | blue | 2 | 20 | 150 | 20 | 170 | 260 | 20 |
| x3426 | 201 | 1551 | 40 | 74 | 76 | red | 1 | 1182 | 20 | 20 | 811 | 20 | 20 |
| x2879 | 202 | 20 | 41 | 8 | 48 | blue | 2 | 190 | 20 | 157 | 233 | 487 | 20 |
| x4269 | 256 | 20 | 42 | 3 | 47 | blue | 2 | 20 | 20 | 125 | 231 | 246 | 223 |
| x4459 | 283 | 20 | 43 | 6 | 46 | blue | 2 | 106 | 406 | 206 | 498 | 954 | 20 |
| x2559 | 305 | 4048 | 44 | 91 | 91 | red | 1 | 20 | 20 | 20 | 699 | 860 | 20 |
| x6633 | 307 | 1440 | 45 | 73 | 73 | red | 1 | 393 | 802 | 772 | 20 | 20 | 20 |
| x4740 | 309 | 1843 | 46 | 79 | 79 | red | 1 | 20 | 20 | 2682 | 678 | 387 | 20 |
| x1315 | 323 | 40 | 47 | 11 | 45 | blue | 2 | 20 | 20 | 20 | 239 | 776 | 20 |
| x4144 | 333 | 4856 | 48 | 92 | 92 | red | 1 | 20 | 20 | 989 | 706 | 20 | 1293 |
| x5780 | 340 | 6305 | 49 | 95 | 97 | red | 1 | 20 | 20 | 20 | 20 | 20 | 20 |
| x5788 | 348 | 43 | 50 | 12 | 43 | blue | 2 | 20 | 310 | 459 | 327 | 1619 | 20 |
| x6266 | 357 | 26 | 51 | 10 | 40 | blue | 2 | 20 | 305 | 175 | 533 | 152 | 297 |

Fig. 8-1

| Gene | ALL41GPT | ALL43GPT | ALL44GPT | ALL45GPT | ALL46GPT | ALL70GPT | ALL73GPT | ALL72GPT | ALL68GPT | ALL69GPT | ALL67GPT | ALL55GPT | ALL56GPT | ALL59GPT |
|---|---|---|---|---|---|---|---|---|---|---|---|---|---|---|
| x4268 | 20 | 20 | 20 | 20 | 20 | 20 | 20 | 20 | 20 | 20 | 20 | 20 | 20 | 20 |
| x3767 | 20 | 20 | 20 | 20 | 20 | 20 | 20 | 20 | 20 | 20 | 20 | 20 | 20 | 20 |
| x5837 | 20 | 20 | 20 | 20 | 20 | 20 | 20 | 20 | 20 | 20 | 20 | 20 | 20 | 109 |
| x4620 | 20 | 20 | 20 | 20 | 20 | 20 | 20 | 20 | 20 | 20 | 378 | 20 | 20 | 20 |
| x1311 | 20 | 7110 | 20 | 20 | 20 | 20 | 20 | 20 | 20 | 20 | 20 | 2102 | 991 | 8693 |
| x857 | 20 | 6598 | 20 | 20 | 20 | 20 | 20 | 20 | 20 | 20 | 20 | 2226 | 453 | 5780 |
| x1504 | 20 | 20 | 20 | 20 | 20 | 20 | 20 | 20 | 20 | 20 | 20 | 20 | 20 | 20 |
| x2862 | 20 | 20 | 20 | 20 | 20 | 20 | 20 | 20 | 1013 | 20 | 20 | 20 | 20 | 20 |
| x1662 | 20 | 20 | 20 | 20 | 20 | 20 | 20 | 20 | 20 | 20 | 20 | 20 | 20 | 20 |
| x4122 | 20 | 20 | 20 | 20 | 20 | 20 | 20 | 20 | 20 | 20 | 295 | 20 | 20 | 20 |
| x984 | 20 | 20 | 20 | 20 | 20 | 20 | 20 | 20 | 20 | 20 | 1986 | 20 | 20 | 20 |
| x6853 | 20 | 20 | 20 | 20 | 20 | 20 | 20 | 20 | 243 | 20 | 20 | 20 | 20 | 20 |
| x5266 | 101 | 20 | 20 | 20 | 20 | 20 | 20 | 20 | 20 | 20 | 20 | 20 | 20 | 20 |
| x2876 | 20 | 20 | 20 | 20 | 20 | 20 | 20 | 20 | 20 | 20 | 20 | 20 | 20 | 20 |
| x350 | 20 | 20 | 20 | 20 | 20 | 20 | 20 | 20 | 20 | 20 | 20 | 20 | 234 | 20 |
| x6583 | 20 | 20 | 20 | 20 | 98 | 98 | 98 | 20 | 20 | 20 | 384 | 20 | 20 | 20 |
| x880 | 20 | 20 | 20 | 20 | 20 | 20 | 20 | 20 | 218 | 236 | 257 | 20 | 20 | 20 |
| x2234 | 73 | 20 | 20 | 20 | 20 | 20 | 244 | 20 | 20 | 20 | 400 | 20 | 20 | 20 |
| x1319 | 20 | 2093 | 20 | 20 | 20 | 20 | 20 | 20 | 20 | 20 | 20 | 20 | 20 | 20 |
| x2330 | 73 | 20 | 20 | 117 | 20 | 20 | 20 | 20 | 20 | 20 | 247 | 159 | 20 | 20 |
| x5263 | 226 | 502 | 20 | 20 | 20 | 117 | 20 | 20 | 20 | 20 | 343 | 20 | 20 | 406 |
| x3221 | 20 | 326 | 20 | 4847 | 20 | 20 | 20 | 279 | 20 | 20 | 269 | 20 | 20 | 20 |
| x2835 | 20 | 2235 | 20 | 20 | 20 | 20 | 20 | 20 | 20 | 20 | 20 | 1767 | 20 | 2724 |
| x6275 | 20 | 20 | 20 | 20 | 20 | 20 | 20 | 20 | 1931 | 20 | 2451 | 20 | 20 | 20 |
| x6019 | 20 | 20 | 20 | 20 | 20 | 20 | 20 | 20 | 20 | 20 | 354 | 20 | 20 | 20 |
| x4287 | 20 | 117 | 20 | 20 | 20 | 20 | 149 | 20 | 104 | 36 | 57 | 20 | 20 | 20 |
| x4230 | 20 | 20 | 20 | 20 | 20 | 20 | 176 | 20 | 20 | 20 | 20 | 20 | 20 | 20 |
| x5827 | 20 | 20 | 174 | 386 | 378 | 20 | 358 | 20 | 20 | 634 | 440 | 20 | 355 | 386 |
| x2970 | 20 | 389 | 20 | 466 | 180 | 20 | 396 | 754 | 648 | 391 | 501 | 20 | 20 | 20 |
| x6775 | 399 | 20 | 20 | 20 | 20 | 20 | 20 | 20 | 1420 | 20 | 20 | 20 | 20 | 20 |
| x3228 | 302 | 4278 | 542 | 20 | 20 | 560 | 20 | 20 | 20 | 20 | 20 | 1068 | 839 | 3439 |
| x5691 | 20 | 132 | 20 | 142 | 213 | 20 | 193 | 173 | 628 | 568 | 219 | 459 | 20 | 20 |
| x7113 | 20 | 20 | 502 | 20 | 20 | 20 | 20 | 453 | 163 | 20 | 2090 | 20 | 20 | 20 |
| x4488 | 184 | 540 | 361 | 330 | 239 | 20 | 63 | 189 | 395 | 513 | 129 | 20 | 20 | 528 |
| x3194 | 20 | 20 | 20 | 20 | 555 | 775 | 981 | 20 | 20 | 20 | 20 | 1445 | 20 | 20 |
| x3532 | 20 | 543 | 20 | 20 | 20 | 20 | 20 | 20 | 20 | 20 | 1433 | 20 | 20 | 20 |
| x5593 | 20 | 165 | 20 | 200 | 20 | 20 | 20 | 94 | 20 | 20 | 20 | 20 | 20 | 20 |
| x862 | 20 | 213 | 20 | 154 | 76 | 119 | 779 | 547 | 298 | 253 | 1384 | 20 | 20 | 20 |
| x855 | 181 | 20 | 20 | 20 | 70 | 20 | 20 | 20 | 214 | 224 | 20 | 20 | 20 | 20 |
| x3426 | 20 | 20 | 20 | 20 | 437 | 20 | 20 | 20 | 20 | 1060 | 20 | 958 | 20 | 20 |
| x2879 | 259 | 20 | 20 | 20 | 20 | 20 | 20 | 20 | 501 | 20 | 20 | 137 | 20 | 20 |
| x4269 | 327 | 20 | 103 | 20 | 210 | 187 | 20 | 166 | 506 | 811 | 138 | 177 | 20 | 20 |
| x4459 | 455 | 218 | 541 | 236 | 477 | 157 | 20 | 20 | 719 | 742 | 20 | 339 | 216 | 556 |
| x2559 | 20 | 20 | 20 | 1034 | 1416 | 20 | 20 | 20 | 958 | 1279 | 1122 | 1178 | 20 | 20 |
| x6633 | 195 | 20 | 20 | 20 | 20 | 334 | 416 | 358 | 239 | 518 | 778 | 446 | 20 | 20 |
| x4740 | 411 | 1745 | 20 | 400 | 20 | 20 | 183 | 474 | 1763 | 316 | 362 | 359 | 20 | 20 |
| x1315 | 167 | 274 | 216 | 236 | 177 | 20 | 20 | 20 | 439 | 607 | 20 | 20 | 20 | 20 |
| x4144 | 20 | 1213 | 20 | 20 | 20 | 917 | 20 | 20 | 20 | 777 | 20 | 2269 | 20 | 2681 |
| x5780 | 20 | 20 | 20 | 20 | 20 | 20 | 1036 | 125 | 245 | 20 | 2147 | 20 | 20 | 20 |
| x5788 | 691 | 341 | 584 | 558 | 932 | 20 | 138 | 20 | 1190 | 713 | 185 | 189 | 375 | 1306 |
| x6266 | 540 | 307 | 123 | 20 | 20 | 433 | 72 | 126 | 768 | 327 | 162 | 144 | 206 | 20 |

Fig. 8-2

| Gene | AML52GPT | AML53GPT | AML51GPT | AML50GPT | AML54GPT | AML57GPT | AML58GPT | AML60GPT | AML61GPT | AML55GPT | AML66GPT | AML63GPT | AML64GPT | AML62GPT |
|---|---|---|---|---|---|---|---|---|---|---|---|---|---|---|
| x4268 | 20 | 20 | 20 | 20 | 20 | 96 | 20 | 20 | 20 | 218 | 20 | 250 | 455 | 333 |
| x3767 | 7213 | 19568 | 9851 | 6595 | 4366 | 10120 | 5903 | 3717 | 2130 | 4667 | 20 | 7924 | 20 | 5249 |
| x5837 | 20 | 357 | 291 | 398 | 20 | 20 | 20 | 20 | 525 | 20 | 73 | 523 | 20 | 20 |
| x4620 | 244 | 20 | 20 | 1057 | 20 | 20 | 20 | 20 | 20 | 403 | 20 | 20 | 20 | 20 |
| x1311 | 20 | 11857 | 5949 | 20 | 21946 | 14957 | 2262 | 38683 | 3423 | 3911 | 20 | 2203 | 20 | 20 |
| x857 | 20 | 12410 | 6177 | 43 | 15963 | 13436 | 1900 | 40792 | 2663 | 2483 | 20 | 1749 | 20 | 20 |
| x1504 | 1178 | 20 | 490 | 316 | 20 | 589 | 20 | 466 | 20 | 499 | 20 | 942 | 20 | 954 |
| x2862 | 1394 | 20 | 20 | 20 | 20 | 20 | 20 | 20 | 20 | 20 | 20 | 2493 | 2415 | 20 |
| x1662 | 3599 | 1465 | 20 | 20 | 1392 | 20 | 1987 | 20 | 20 | 1336 | 20 | 6155 | 20 | 3308 |
| x4122 | 20 | 1522 | 1426 | 412 | 20 | 20 | 333 | 20 | 5256 | 5254 | 20 | 494 | 20 | 20 |
| x984 | 1704 | 2867 | 20 | 20 | 1986 | 1507 | 20 | 2134 | 20 | 20 | 20 | 20 | 20 | 20 |
| x6853 | 319 | 20 | 343 | 400 | 20 | 20 | 20 | 20 | 242 | 1160 | 20 | 20 | 20 | 20 |
| x5266 | 20 | 177 | 102 | 227 | 194 | 121 | 290 | 20 | 20 | 20 | 20 | 500 | 20 | 437 |
| x2876 | 20 | 522 | 788 | 654 | 20 | 20 | 20 | 20 | 20 | 20 | 20 | 20 | 20 | 20 |
| x350 | 232 | 20 | 339 | 1213 | 215 | 20 | 20 | 20 | 20 | 20 | 20 | 20 | 1417 | 20 |
| x6583 | 20 | 945 | 915 | 753 | 20 | 20 | 20 | 20 | 20 | 20 | 20 | 20 | 1504 | 847 |
| x880 | 20 | 20 | 826 | 440 | 20 | 20 | 20 | 20 | 20 | 20 | 332 | 20 | 20 | 20 |
| x2234 | 20 | 854 | 1062 | 924 | 20 | 20 | 20 | 20 | 20 | 20 | 69 | 20 | 20 | 20 |
| x1319 | 20 | 20 | 20 | 20 | 20 | 20 | 20 | 20 | 20 | 20 | 830 | 20 | 20 | 20 |
| x2330 | 1533 | 759 | 593 | 928 | 629 | 827 | 646 | 336 | 526 | 560 | 341 | 1883 | 2204 | 1605 |
| x5263 | 9433 | 850 | 995 | 3871 | 2241 | 2010 | 1483 | 4177 | 20 | 1347 | 20 | 7807 | 658 | 6913 |
| x3221 | 2936 | 666 | 50 | 1104 | 2085 | 656 | 1567 | 854 | 600 | 6927 | 20 | 19653 | 20 | 5657 |
| x2835 | 1676 | 13774 | 17279 | 11036 | 15196 | 28647 | 2571 | 25625 | 2297 | 4561 | 20 | 2270 | 2914 | 1255 |
| x6275 | 2007 | 3870 | 2335 | 5814 | 4403 | 2287 | 2871 | 2122 | 3156 | 2194 | 543 | 5949 | 4174 | 7133 |
| x6019 | 20 | 520 | 5885 | 2247 | 20 | 20 | 216 | 20 | 227 | 542 | 20 | 255 | 1344 | 20 |
| x4287 | 393 | 84 | 60 | 241 | 20 | 20 | 20 | 20 | 91 | 322 | 297 | 64 | 20 | 99 |
| x4230 | 217 | 1353 | 1051 | 1163 | 20 | 432 | 510 | 20 | 413 | 454 | 20 | 275 | 1266 | 20 |
| x5827 | 407 | 579 | 494 | 1137 | 20 | 534 | 20 | 20 | 483 | 617 | 20 | 20 | 1054 | 1466 |
| x2970 | 442 | 4460 | 683 | 729 | 458 | 20 | 20 | 20 | 20 | 20 | 410 | 656 | 1152 | 676 |
| x6775 | 20 | 942 | 416 | 764 | 20 | 243 | 20 | 20 | 20 | 20 | 20 | 20 | 729 | 718 |
| x3228 | 1174 | 24214 | 5754 | 1934 | 988 | 5037 | 20 | 8929 | 20 | 20 | 20 | 20 | 2738 | 1014 |
| x5691 | 313 | 3546 | 788 | 2299 | 589 | 428 | 525 | 507 | 652 | 339 | 20 | 1318 | 1130 | 924 |
| x7113 | 17846 | 21404 | 2745 | 11686 | 10737 | 3168 | 14193 | 2460 | 20 | 12735 | 2103 | 19680 | 3293 | 24178 |
| x4488 | 20 | 20 | 20 | 139 | 20 | 20 | 20 | 99 | 106 | 20 | 80 | 123 | 20 | 20 |
| x3194 | 20 | 20 | 20 | 1531 | 2104 | 1816 | 3072 | 1498 | 20 | 20 | 745 | 3983 | 13798 | 6065 |
| x3532 | 10274 | 1320 | 20 | 1620 | 1289 | 890 | 2021 | 597 | 20 | 807 | 365 | 8485 | 20 | 7395 |
| x5593 | 892 | 1233 | 1269 | 1582 | 643 | 1267 | 1480 | 1568 | 3166 | 1550 | 163 | 2757 | 1415 | 1121 |
| x862 | 914 | 963 | 2186 | 1446 | 260 | 20 | 284 | 328 | 728 | 1171 | 243 | 1157 | 382 | 375 |
| x855 | 20 | 248 | 20 | 20 | 20 | 119 | 20 | 20 | 78 | 20 | 20 | 20 | 634 | 20 |
| x3426 | 20 | 1622 | 3049 | 3818 | 3491 | 2450 | 2101 | 5389 | 8921 | 908 | 20 | 1409 | 20 | 20 |
| x2879 | 20 | 173 | 20 | 20 | 20 | 20 | 20 | 20 | 119 | 20 | 20 | 20 | 767 | 345 |
| x4269 | 20 | 100 | 20 | 20 | 20 | 31 | 20 | 20 | 43 | 20 | 410 | 20 | 20 | 20 |
| x4459 | 20 | 20 | 20 | 20 | 20 | 20 | 20 | 309 | 20 | 20 | 20 | 20 | 20 | 20 |
| x2559 | 5308 | 2574 | 2397 | 3857 | 1872 | 2547 | 3239 | 1700 | 20 | 2052 | 20 | 9980 | 20 | 7131 |
| x6633 | 1021 | 1212 | 20 | 2599 | 696 | 623 | 995 | 444 | 509 | 345 | 20 | 2063 | 1580 | 1962 |
| x4740 | 1063 | 781 | 1512 | 1846 | 1834 | 442 | 20 | 3819 | 834 | 1343 | 715 | 867 | 778 | 428 |
| x1315 | 20 | 20 | 20 | 20 | 20 | 20 | 20 | 20 | 20 | 20 | 20 | 20 | 20 | 20 |
| x4144 | 747 | 9006 | 10171 | 9138 | 22222 | 9986 | 14230 | 27285 | 28390 | 17371 | 20 | 5895 | 3917 | 2606 |
| x5780 | 20 | 3628 | 19878 | 9620 | 20 | 20 | 661 | 20 | 5864 | 2964 | 20 | 2531 | 73 | 20 |
| x5788 | 201 | 320 | 20 | 405 | 646 | 206 | 20 | 320 | 147 | 22 | 20 | 20 | 932 | 20 |
| x6266 | 20 | 20 | 20 | 20 | 20 | 20 | 20 | 209 | 156 | 20 | 20 | 205 | 20 | 210 |

Fig. 8-3

| Gene | ALLTMean | AMLTMean | ALLTRANK | AMLTRANK | DIFFTRANK | COLORT$ | Symbol | ALL39GPT | ALL40GPT | ALL42GPT | ALL47GPT | ALL48GPT | ALL49GPT |
|---|---|---|---|---|---|---|---|---|---|---|---|---|---|
| x5833 | 359 | 45 | 52 | 14 | 42 | blue | 2 | 333 | 20 | 471 | 20 | 648 | 20 |
| x4505 | 369 | 65 | 53 | 17 | 44 | blue | 2 | 20 | 20 | 293 | 498 | 905 | 20 |
| x4822 | 370 | 1812 | 54 | 78 | 78 | red | 1 | 20 | 797 | 265 | 313 | 178 | 390 |
| x2196 | 419 | 102 | 55 | 21 | 41 | blue | 2 | 260 | 20 | 210 | 327 | 582 | 20 |
| x5497 | 428 | 90 | 56 | 20 | 39 | blue | 2 | 20 | 20 | 272 | 355 | 816 | 274 |
| x3540 | 453 | 5144 | 57 | 94 | 93 | red | 1 | 20 | 20 | 20 | 1405 | 20 | 20 |
| x5937 | 456 | 86 | 58 | 19 | 38 | blue | 2 | 20 | 497 | 20 | 20 | 584 | 20 |
| x6817 | 498 | 24 | 59 | 9 | 34 | blue | 2 | 20 | 718 | 20 | 508 | 691 | 20 |
| x4188 | 513 | 2532 | 60 | 86 | 83 | red | 1 | 20 | 360 | 911 | 605 | 920 | 20 |
| x6856 | 519 | 146 | 61 | 26 | 37 | blue | 2 | 193 | 20 | 237 | 462 | 1132 | 313 |
| x5151 | 538 | 45 | 62 | 15 | 33 | blue | 2 | 475 | 251 | 362 | 493 | 951 | 356 |
| x3504 | 607 | 149 | 63 | 27 | 36 | blue | 2 | 642 | 20 | 548 | 371 | 1149 | 793 |
| x793 | 625 | 166 | 64 | 29 | 35 | blue | 2 | 20 | 813 | 356 | 682 | 615 | 20 |
| x6952 | 670 | 149 | 65 | 28 | 32 | blue | 2 | 374 | 453 | 602 | 502 | 2063 | 705 |
| x709 | 785 | 10479 | 66 | 100 | 100 | red | 1 | 741 | 20 | 1012 | 197 | 20 | 206 |
| x6351 | 786 | 230 | 67 | 32 | 31 | blue | 2 | 490 | 865 | 409 | 777 | 2097 | 72 |
| x6536 | 861 | 126 | 68 | 22 | 26 | blue | 2 | 786 | 994 | 233 | 510 | 598 | 861 |
| x2277 | 896 | 171 | 69 | 30 | 28 | blue | 2 | 20 | 382 | 553 | 638 | 1340 | 799 |
| x6448 | 917 | 134 | 70 | 24 | 25 | blue | 2 | 20 | 1526 | 771 | 558 | 2695 | 1055 |
| x543 | 930 | 246 | 71 | 35 | 29 | blue | 2 | 637 | 860 | 539 | 546 | 1627 | 464 |
| x635 | 982 | 315 | 72 | 41 | 30 | blue | 2 | 20 | 828 | 583 | 1199 | 2177 | 991 |
| x81 | 1009 | 276 | 73 | 38 | 27 | blue | 2 | 613 | 566 | 897 | 481 | 2385 | 917 |
| x6108 | 1056 | 20 | 74 | 7 | 22 | blue | 2 | 20 | 20 | 20 | 617 | 20 | 20 |
| x5404 | 1067 | 3767 | 75 | 90 | 88 | red | 1 | 1018 | 128 | 1726 | 1092 | 1415 | 521 |
| x6781 | 1078 | 20 | 76 | 5 | 21 | blue | 2 | 20 | 3771 | 416 | 20 | 671 | 20 |
| x4520 | 1106 | 20 | 77 | 1 | 19 | blue | 2 | 784 | 322 | 20 | 306 | 1560 | 360 |
| x2956 | 1203 | 383 | 78 | 44 | 24 | blue | 2 | 2112 | 1323 | 826 | 613 | 1475 | 1353 |
| x4983 | 1230 | 80 | 79 | 18 | 18 | blue | 2 | 837 | 20 | 20 | 575 | 603 | 763 |
| x3478 | 1306 | 379 | 80 | 43 | 23 | blue | 2 | 4048 | 879 | 1140 | 20 | 1355 | 1816 |
| x7086 | 1311 | 239 | 81 | 33 | 20 | blue | 2 | 1484 | 606 | 1751 | 1052 | 2428 | 1467 |
| x3008 | 1399 | 6939 | 82 | 97 | 96 | red | 1 | 803 | 480 | 2635 | 983 | 298 | 2081 |
| x6601 | 1411 | 253 | 83 | 36 | 17 | blue | 2 | 176 | 490 | 678 | 1903 | 2123 | 424 |
| x3680 | 1643 | 7109 | 84 | 98 | 95 | red | 1 | 20 | 1269 | 1045 | 2450 | 1537 | 690 |
| x2969 | 1705 | 293 | 85 | 40 | 16 | blue | 2 | 306 | 759 | 727 | 2582 | 3482 | 1146 |
| x7129 | 1844 | 241 | 86 | 34 | 14 | blue | 2 | 753 | 2941 | 412 | 361 | 810 | 1582 |
| x5116 | 2021 | 440 | 87 | 49 | 15 | blue | 2 | 2264 | 1102 | 1125 | 888 | 3629 | 881 |
| x1435 | 2198 | 281 | 88 | 39 | 12 | blue | 2 | 2131 | 320 | 1681 | 1748 | 3079 | 2427 |
| x2567 | 2219 | 320 | 89 | 42 | 13 | blue | 2 | 939 | 502 | 559 | 508 | 1200 | 6273 |
| x1824 | 2390 | 386 | 90 | 45 | 11 | blue | 2 | 1178 | 20 | 20 | 1836 | 4594 | 2114 |
| x3654 | 2879 | 55 | 91 | 16 | 9 | blue | 2 | 20 | 20 | 20 | 298 | 20 | 529 |
| x1635 | 3022 | 135 | 92 | 25 | 7 | blue | 2 | 8700 | 4614 | 4357 | 7369 | 7216 | 6603 |
| x307 | 3467 | 20 | 93 | 4 | 4 | blue | 2 | 12968 | 20 | 4750 | 2559 | 5632 | 9288 |
| x1519 | 3829 | 274 | 94 | 37 | 3 | blue | 2 | 3633 | 20 | 5358 | 1338 | 8921 | 4174 |
| x1837 | 3863 | 674 | 95 | 55 | 6 | blue | 2 | 2037 | 1497 | 2105 | 2805 | 6996 | 2753 |
| x2019 | 3872 | 1157 | 96 | 66 | 10 | blue | 2 | 4057 | 1585 | 3600 | 2425 | 7275 | 2787 |
| x1634 | 4213 | 1365 | 97 | 72 | 8 | blue | 2 | 4101 | 2427 | 2003 | 2893 | 9908 | 4020 |
| x1069 | 4361 | 1138 | 98 | 65 | 5 | blue | 2 | 4646 | 2141 | 3090 | 3198 | 10565 | 5279 |
| x5545 | 6382 | 1961 | 99 | 81 | 2 | blue | 2 | 6199 | 20 | 11483 | 2372 | 11886 | 740 |
| x5348 | 6785 | 1743 | 100 | 77 | 1 | blue | 2 | 4142 | 1462 | 2208 | 3681 | 7756 | 4813 |

Fig. 8-4

| Gene | ALL41GPT | ALL43GPT | ALL44GPT | ALL45GPT | ALL46GPT | ALL70GPT | ALL73GPT | ALL72GPT | ALL68GPT | ALL69GPT | ALL67GPT | ALL55GPT | ALL56GPT | ALL59GPT |
|---|---|---|---|---|---|---|---|---|---|---|---|---|---|---|
| x5833 | 428 | 20 | 346 | 264 | 283 | 349 | 353 | 502 | 517 | 596 | 223 | 177 | 337 | 20 |
| x4505 | 463 | 237 | 339 | 20 | 20 | 20 | 198 | 231 | 577 | 403 | 211 | 431 | 177 | 302 |
| x4822 | 491 | 20 | 20 | 20 | 173 | 426 | 190 | 406 | 462 | 505 | 1448 | 217 | 184 | 20 |
| x2196 | 360 | 293 | 234 | 20 | 187 | 20 | 224 | 418 | 523 | 387 | 223 | 272 | 309 | 20 |
| x5497 | 530 | 20 | 320 | 129 | 245 | 218 | 161 | 179 | 859 | 577 | 194 | 237 | 20 | 322 |
| x3540 | 20 | 20 | 20 | 20 | 1750 | 20 | 20 | 20 | 20 | 20 | 2718 | 20 | 1815 | 20 |
| x5937 | 521 | 20 | 20 | 20 | 20 | 284 | 474 | 666 | 1108 | 766 | 324 | 376 | 20 | 20 |
| x6817 | 745 | 20 | 20 | 781 | 220 | 123 | 792 | 233 | 1263 | 709 | 20 | 836 | 427 | 449 |
| x4188 | 565 | 216 | 289 | 1110 | 291 | 20 | 187 | 435 | 1053 | 799 | 1616 | 646 | 417 | 20 |
| x6856 | 665 | 401 | 484 | 317 | 259 | 20 | 227 | 401 | 888 | 630 | 483 | 224 | 417 | 20 |
| x5151 | 616 | 329 | 710 | 467 | 475 | 348 | 218 | 493 | 580 | 573 | 200 | 439 | 20 | 593 |
| x3504 | 403 | 259 | 492 | 317 | 480 | 443 | 264 | 439 | 1034 | 1290 | 227 | 604 | 932 | 447 |
| x793 | 633 | 499 | 468 | 1075 | 408 | 334 | 264 | 20 | 927 | 982 | 20 | 344 | 494 | 20 |
| x6952 | 632 | 266 | 20 | 20 | 628 | 431 | 271 | 350 | 768 | 1112 | 371 | 352 | 350 | 343 |
| x709 | 20 | 20 | 20 | 149 | 20 | 236 | 2525 | 257 | 257 | 20 | 5830 | 20 | 20 | 20 |
| x6351 | 640 | 877 | 1042 | 1468 | 586 | 826 | 352 | 457 | 1106 | 1417 | 384 | 509 | 824 | 1156 |
| x6536 | 615 | 853 | 773 | 382 | 443 | 344 | 1164 | 894 | 1226 | 765 | 519 | 421 | 1359 | 739 |
| x2277 | 707 | 562 | 575 | 747 | 392 | 334 | 146 | 235 | 1385 | 1012 | 140 | 339 | 496 | 20 |
| x6448 | 521 | 706 | 504 | 368 | 704 | 433 | 675 | 497 | 1474 | 1644 | 448 | 486 | 512 | 1797 |
| x543 | 668 | 629 | 800 | 679 | 457 | 533 | 471 | 986 | 1690 | 1211 | 20 | 431 | 502 | 754 |
| x635 | 857 | 1004 | 972 | 711 | 557 | 680 | 223 | 294 | 1238 | 1392 | 20 | 521 | 906 | 968 |
| x81 | 1106 | 1156 | 1294 | 938 | 779 | 293 | 915 | 1757 | 2357 | 1767 | 20 | 549 | 350 | 640 |
| x6108 | 20 | 20 | 20 | 20 | 20 | 737 | 1115 | 20 | 1007 | 826 | 976 | 20 | 1104 | 20 |
| x5404 | 961 | 612 | 554 | 3889 | 1524 | 2111 | 3808 | 1976 | 4178 | 2570 | 3570 | 319 | 20 | 424 |
| x6781 | 256 | 329 | 1365 | 567 | 589 | 567 | 20 | 931 | 672 | 886 | 20 | 464 | 20 | 793 |
| x4520 | 532 | 978 | 336 | 753 | 639 | 1140 | 2277 | 990 | 445 | 2268 | 20 | 20 | 793 | 1154 |
| x2956 | 1033 | 937 | 1691 | 479 | 438 | 1002 | 1504 | 1926 | 1088 | 1187 | 1661 | 751 | 1127 | 846 |
| x4983 | 770 | 20 | 579 | 444 | 570 | 853 | 1213 | 586 | 1235 | 1284 | 908 | 20 | 1009 | 310 |
| x3478 | 1147 | 605 | 1749 | 795 | 521 | 693 | 1312 | 2352 | 1131 | 1187 | 1295 | 911 | 1521 | 950 |
| x7086 | 1479 | 2148 | 1955 | 1275 | 980 | 1277 | 828 | 1361 | 3923 | 1794 | 929 | 821 | 1297 | 1087 |
| x3008 | 1167 | 4451 | 1529 | 20 | 701 | 2052 | 876 | 343 | 2068 | 969 | 3050 | 3360 | 1977 | 3764 |
| x6601 | 1258 | 699 | 1236 | 555 | 384 | 490 | 149 | 583 | 1700 | 808 | 581 | 723 | 834 | 618 |
| x3680 | 1183 | 7054 | 155 | 1327 | 283 | 348 | 1128 | 1357 | 2282 | 2128 | 4401 | 2057 | 1102 | 4509 |
| x2969 | 1657 | 1802 | 2345 | 1407 | 798 | 1072 | 227 | 325 | 2869 | 1569 | 20 | 1145 | 1148 | 734 |
| x7129 | 2380 | 2894 | 342 | 389 | 464 | 3688 | 2630 | 2636 | 503 | 5009 | 358 | 1088 | 857 | 20 |
| x5116 | 1022 | 1074 | 1819 | 1058 | 1355 | 1373 | 2160 | 2015 | 20 | 688 | 1358 | 20 | 697 | 1344 |
| x1435 | 1477 | 557 | 1577 | 530 | 1103 | 1004 | 1918 | 1469 | 2553 | 2698 | 1918 | 426 | 2054 | 3868 |
| x2567 | 7097 | 1144 | 1695 | 1479 | 1594 | 1169 | 2810 | 2486 | 1968 | 5448 | 479 | 664 | 1060 | 676 |
| x1824 | 3714 | 2004 | 1934 | 2532 | 3331 | 5598 | 1789 | 746 | 3650 | 8399 | 884 | 3282 | 2989 | 3983 |
| x3654 | 360 | 20 | 20 | 20 | 20 | 20 | 417 | 2278 | 698 | 331 | 1205 | 3901 | 416 | 525 | 
| x1635 | 1487 | 7560 | 8791 | 12307 | 5433 | 1644 | 1671 | 1327 | 5653 | 4830 | 20 | 1595 | 4537 | 7480 |
| x307 | 3627 | 3115 | 11999 | 4200 | 3403 | 4896 | 4317 | 6517 | 6101 | 4634 | 707 | 1642 | 4941 | 2282 |
| x1519 | 6400 | 3598 | 5600 | 7477 | 6841 | 1814 | 1608 | 2420 | 6203 | 9155 | 2474 | 3375 | 2417 | 7867 |
| x1837 | 4240 | 3821 | 3686 | 2943 | 2809 | 2178 | 306 | 1374 | 8402 | 5032 | 1358 | 1188 | 2075 | 4961 |
| x2019 | 3367 | 2271 | 5083 | 2621 | 2388 | 1768 | 2097 | 5088 | 4787 | 5499 | 7408 | 2626 | 3229 | 2620 |
| x1634 | 4306 | 2600 | 3423 | 2886 | 2955 | 2490 | 1427 | 3263 | 5549 | 5098 | 1799 | 2219 | 2603 | 3739 |
| x1069 | 3686 | 3619 | 5420 | 3770 | 3972 | 2962 | 1076 | 3102 | 6609 | 6622 | 1438 | 2833 | 648 | 4912 |
| x5545 | 5251 | 8420 | 2266 | 2362 | 4824 | 1288 | 13146 | 10156 | 9009 | 10965 | 1133 | 1997 | 2178 | 2122 |
| x5348 | 4714 | 3922 | 1850 | 4662 | 2931 | 3765 | 1826 | 2694 | 9487 | 5149 | 1365 | 2506 | 3777 | 5104 |

Fig. 8-5

| Gene | AML52GPT | AML53GPT | AML51GPT | AML50GPT | AML54GPT | AML57GPT | AML58GPT | AML60GPT | AML61GPT | AML55GPT | AML66GPT | AML63GPT | AML64GPT | AML62GPT |
|---|---|---|---|---|---|---|---|---|---|---|---|---|---|---|
| x5833 | 20 | 284 | 112 | 20 | 20 | 20 | 20 | 20 | 307 | 20 | 20 | 233 | 20 | 20 |
| x4505 | 101 | 433 | 362 | 313 | 470 | 290 | 20 | 206 | 20 | 20 | 254 | 230 | 956 | 236 |
| x4822 | 1744 | 1522 | 2089 | 2735 | 855 | 444 | 1020 | 385 | 489 | 716 | 460 | 2686 | 1499 | 1837 |
| x2196 | 20 | 548 | 20 | 244 | 20 | 20 | 20 | 228 | 20 | 20 | 165 | 294 | 374 | 340 |
| x5497 | 20 | 20 | 20 | 286 | 20 | 20 | 20 | 279 | 20 | 204 | 393 | 20 | 680 | 20 |
| x3540 | 13422 | 5946 | 20 | 6223 | 6179 | 5971 | 3913 | 2442 | 20 | 20 | 20 | 6215 | 11451 | 7323 |
| x5937 | 98 | 678 | 20 | 207 | 20 | 20 | 20 | 20 | 20 | 20 | 328 | 429 | 20 | 20 |
| x6817 | 20 | 20 | 20 | 20 | 721 | 528 | 20 | 796 | 20 | 20 | 160 | 214 | 365 | 20 |
| x4188 | 3016 | 3162 | 1518 | 3223 | 5704 | 2458 | 1724 | 2496 | 1705 | 1717 | 1095 | 6008 | 1819 | 3785 |
| x6856 | 20 | 154 | 130 | 20 | 369 | 273 | 204 | 410 | 20 | 297 | 20 | 305 | 295 | 271 |
| x5151 | 248 | 20 | 20 | 20 | 20 | 20 | 20 | 20 | 20 | 198 | 225 | 20 | 20 | 20 |
| x3504 | 344 | 140 | 94 | 20 | 734 | 300 | 20 | 536 | 585 | 20 | 216 | 695 | 401 | 498 |
| x793 | 20 | 20 | 20 | 20 | 20 | 491 | 20 | 607 | 472 | 356 | 217 | 530 | 932 | 493 |
| x6952 | 20 | 635 | 283 | 326 | 689 | 20 | 20 | 20 | 533 | 360 | 543 | 452 | 647 | 180 |
| x709 | 593 | 8252 | 20459 | 13144 | 20 | 20 | 2132 | 20 | 13968 | 7229 | 621 | 9612 | 2667 | 322 |
| x6351 | 144 | 20 | 20 | 20 | 846 | 239 | 20 | 350 | 20 | 231 | 236 | 1109 | 20 | 553 |
| x6536 | 20 | 109 | 48 | 20 | 352 | 20 | 20 | 20 | 20 | 220 | 20 | 20 | 195 | 282 |
| x2277 | 163 | 135 | 126 | 225 | 413 | 20 | 20 | 412 | 422 | 20 | 362 | 462 | 20 | 384 |
| x6448 | 892 | 20 | 20 | 20 | 20 | 363 | 785 | 647 | 20 | 20 | 20 | 766 | 2724 | 528 |
| x543 | 495 | 20 | 168 | 176 | 310 | 222 | 287 | 769 | 20 | 20 | 228 | 1018 | 249 | 1047 |
| x635 | 260 | 20 | 20 | 296 | 1008 | 404 | 312 | 628 | 20 | 227 | 530 | 949 | 509 | 929 |
| x81 | 612 | 221 | 20 | 20 | 1130 | 20 | 618 | 20 | 281 | 308 | 20 | 3044 | 20 | 1695 |
| x6108 | 20 | 20 | 20 | 20 | 20 | 20 | 20 | 20 | 20 | 20 | 20 | 20 | 20 | 20 |
| x5404 | 1066 | 4766 | 3702 | 2996 | 1150 | 455 | 1533 | 494 | 5487 | 7003 | 1141 | 3392 | 3074 | 2787 |
| x6781 | 20 | 484 | 20 | 20 | 20 | 20 | 20 | 20 | 20 | 20 | 20 | 20 | 20 | 20 |
| x4520 | 20 | 20 | 20 | 628 | 721 | 20 | 20 | 20 | 20 | 20 | 20 | 459 | 3047 | 20 |
| x2956 | 250 | 367 | 382 | 190 | 578 | 398 | 20 | 486 | 485 | 588 | 669 | 745 | 878 | 625 |
| x4983 | 20 | 20 | 416 | 20 | 20 | 20 | 20 | 20 | 20 | 20 | 20 | 20 | 20 | 20 |
| x3478 | 20 | 1024 | 20 | 802 | 20 | 534 | 534 | 371 | 1092 | 20 | 625 | 832 | 818 | 349 |
| x7086 | 139 | 368 | 20 | 197 | 20 | 196 | 20 | 461 | 446 | 375 | 528 | 253 | 450 | 328 |
| x3008 | 15202 | 7982 | 4980 | 6808 | 1867 | 2114 | 11007 | 4193 | 3017 | 2906 | 945 | 7392 | 891 | 14347 |
| x6601 | 401 | 20 | 20 | 148 | 784 | 330 | 20 | 919 | 20 | 20 | 1082 | 810 | 544 | 748 |
| x3680 | 6371 | 7056 | 6957 | 7281 | 7248 | 8964 | 3653 | 10449 | 975 | 5086 | 3340 | 5178 | 6311 | 5314 |
| x2969 | 882 | 20 | 249 | 185 | 2110 | 807 | 20 | 1235 | 773 | 501 | 993 | 1425 | 20 | 919 |
| x7129 | 20 | 653 | 422 | 20 | 20 | 20 | 20 | 20 | 20 | 20 | 20 | 20 | 20 | 810 |
| x5116 | 20 | 1538 | 20 | 20 | 1234 | 20 | 20 | 980 | 1415 | 995 | 904 | 20 | 20 | 968 |
| x1435 | 541 | 193 | 537 | 219 | 1546 | 1271 | 250 | 704 | 2007 | 675 | 1162 | 20 | 2789 | 1524 |
| x2567 | 20 | 675 | 20 | 396 | 377 | 60 | 145 | 20 | 281 | 20 | 399 | 558 | 710 | 933 |
| x1824 | 20 | 20 | 372 | 20 | 20 | 149 | 1394 | 953 | 1586 | 1357 | 997 | 20 | 20 | 20 |
| x3654 | 20 | 20 | 20 | 20 | 20 | 20 | 612 | 20 | 20 | 20 | 425 | 20 | 20 | 500 |
| x1635 | 20 | 20 | 20 | 20 | 20 | 20 | 20 | 445 | 20 | 20 | 20 | 20 | 20 | 20 |
| x307 | 20 | 20 | 20 | 20 | 20 | 20 | 698 | 20 | 20 | 20 | 20 | 20 | 20 | 1742 |
| x1519 | 1342 | 20 | 20 | 20 | 20 | 20 | 20 | 20 | 20 | 20 | 836 | 20 | 20 | 20 |
| x1837 | 407 | 2585 | 376 | 1238 | 2685 | 2295 | 562 | 2564 | 934 | 427 | 834 | 537 | 3201 | 417 |
| x2019 | 649 | 4118 | 20 | 815 | 20 | 20 | 1696 | 870 | 2704 | 1476 | 819 | 1427 | 20 | 1621 |
| x1634 | 995 | 2027 | 1142 | 1456 | 1463 | 1585 | 1072 | 1417 | 1153 | 1084 | 2175 | 1598 | 3494 | 1554 |
| x1069 | 1439 | 666 | 764 | 1683 | 1629 | 469 | 420 | 1151 | 1012 | 614 | 2284 | 1453 | 986 | 720 |
| x5545 | 778 | 4537 | 820 | 1527 | 787 | 715 | 744 | 678 | 20 | 2752 | 1356 | 1863 | 2152 | 1276 |
| x5348 | 1027 | 6330 | 1319 | 1243 | 648 | 1004 | 1845 | 1162 | 1636 | 2583 | 11056 | 1562 | 8883 | 2082 |

Fig. 8-6

METHOD AND DISPLAY FOR MULTIVARIATE CLASSIFICATION

RELATED APPLICATIONS

This application claims benefit under 35 U.S.C. §119 of U.S. provisional application Ser. No. 60/240,403, filed Oct. 13, 2000, and of U.S. provisional application Ser. No. 60/252,290, filed Nov. 21, 2000.

FIELD OF THE INVENTION

The invention relates to methods of classifying tissues based on multivariate data for diagnostic, prognostic or therapeutic purposes. The invention also relates to methods and user interfaces for displaying such multivariate data to facilitate rapid decision making.

BACKGROUND OF THE INVENTION

Classification of tissues historically depended on an examination of the gross morphology and histology of the tissues. The inadequacy of these methods for classification of tissues that are similar in appearance, such as different tumors arising from the same tissue or organ, is known. More recently, methods of tissue analysis and classification have been developed that rely on genetic analysis of tissues. While these genetic analytical methods are more powerful for distinguishing tissue types, and are simple to practice, the methods also generated quantities of data that are orders of magnitude greater than classical histology methods. For example, gene expression profiling of tissues by the application of microarray technology determines simultaneously the expression of thousands of genes. The challenge of identifying the data useful in tissue classification from the raw data is a problem that requires a solution that can be applied in clinical settings. Present statistical and data display methods are not satisfactory for this application.

Thus it is of key importance in analytical processes for classification of unknown tissues reduce large quantities of multivariate data to a quantity that can be readily analyzed. A typical treatment of multivariate data is to generate binary statistics known to those in the art. For example, a binary regression of two data sets associated with two objects will produce a statistical relationship between the two objects within a statistical confidence.

Prior art data analysis tools have focused on describing objects of diagnostic relevance to exhaustion, which in turn relied on using binary statistical methods to "collapse" large volumes of data for decision making. These methodologies suffer from a requirement for sophisticated analysis and interpretation by the end user. The prior art approaches thus lack methods for analyzing large quantities of multivariate data using statistically proven methods, yet providing for ready interpretation of the data.

Highly parallel quantitative measurement systems are increasingly available for analysis of complex biological systems, but practical data reduction systems limit application. For example, microarray (RNA) expression analysis is used for phenotyping of human tissues; quantitative measurement of thousands of RNAs ("variables") in a single tissue ("object") is used to assign group membership ("classify"). Typically, a very large number of variables are measured in a training set of two different tissues, and a subset of variables which best distinguishes the two tissue types is identified through some statistical process. This can yield dozens, or even hundreds, of variables which are individually imperfect, but collectively effective, for classification of future (test) objects which were not part of the training set.

Once a predictive model is constructed from a suitable training set, it is desirable to have a simple method to generalize this model to a variety of variable measurement systems (different manufacturer's gene arrays, for example). This is not readily possible if the different platforms have independent units of measurement, and different sensitivity thresholds. Diagnostic and prognostic evaluation of tissues is hampered by this cross-platform incompatibility. Similar problems exist with respect to sample-to-sample, run-to-run and user-to-user variability when using the same device or an identical device.

In addition, the variables are not easily evaluated for any sample, even with the training set data as a comparison. For example, gene expression data frequently is provided as a table describing the increases in expression of the set of genes. This type of display requires the end user to compare large sets of data for the expression of multiple genes and make judgments as to the phenotype of a tissue based on these multiple parameters. Accordingly, there is a need to develop methods of obtaining and analyzing data that describe a tissue more accurately and more precisely for diagnostic evaluation. Further, there is a need for methods of displaying multivariate data without reference to the specific units of data generated by specific analytical devices. There also is a need for methods and devices to display the data for rapid and simplified evaluation by end users, particularly in a clinical setting.

SUMMARY OF THE INVENTION

The present invention represents a new approach to data analysis for multivariate classification, particularly as used in medical diagnostics. The invention is in part an intuitive decision making tool for rapid classification of "objects" (e.g., cell, tissue or tumor samples) from evaluation of many simultaneous "variables" (e.g., quantitative gene expression profiles). The data analysis methods of the invention provide the end user with a simplified and robust output for diagnostic classification of objects based on identifying and evaluating multiple variables of predetermined diagnostic relevance. The raw data generated by analysis of the variables is transformed by application or appropriate algorithms to scaleless rank differentials between the variables. The rank orders of variables are used to classify tissues based on readily observable user interfaces, such as a graphical (e.g., visual) user interface or an auditory user interface.

According to one aspect of the invention, methods of classifying an object are provided. The methods include the steps of measuring, among one or more samples of the object, values of a plurality of variables associated with the object; selecting one or more of the plurality of variables by which the object may be identified; and representing the object by the one or more variables.

In certain embodiments, the step of selecting includes selecting the one or more variables on the basis of a difference between values of the variables and values of variables of another object. In other embodiments, the step of selecting further comprises steps of comparing the values of the plurality of variables with values of a plurality of variables associated with another object and selecting the one or more of the variables by which the object may be identified in response to the comparing step. Preferably the object is a tissue, and the step of measuring comprises microarray expression phenotyping the tissue.

In additional embodiments, the step of selecting comprises calculating mean values of variables among variables of two groups; comparing the mean values; and selecting the one or more of the variables by which the object may be identified in response to the comparing step. The step of selecting also can include ordering the variables according to the calculated mean values. Preferably the step of ordering comprises normalizing values of the variables to a predetermined range.

According to another aspect of the invention, additional methods of classifying an object are provided. The methods include steps of calculating a rank order associated with index set values (TRANK); calculating a second rank order associated with the difference of index and contrasting set values (DIFFTRAN); calculating index set means (ALLTMEAN); and comparing these rank orders and means to previously indexed objects. In certain embodiments the methods include displaying, to a user, a visual indication of a relationship described by the rank orders. Preferably, the visual indication is a ternary plot.

According to still another aspect of the invention, methods of characterizing data sets containing multiple variables are provided. The methods include statistically determining a subset of the variables to describe a difference between the data sets; in a first set of data, ranking each of the variables in the subset of variables according to its numerical value in the first set of data; calculating a difference for each of the variables in the subset of variables between the first set of data and a second set of data; and ranking each of the variables in the subset of the variables according to the difference for each of the variables in the subset of variables. Preferably the methods include displaying the subset of variables of the first set of data according the rankings of each variable of the subset.

Methods for rendering, to a user, a computer interface are provided in other aspects of the invention. The methods include obtaining a set of variables associated with an object; reducing the set of variables to a subset of variables, which are associated with the object by a predetermined parameter; ranking each of the variables in the subset of variables according to their numerical value; and applying a computer interface associated with a human sense. In some embodiments, the human sense is hearing, vision, and touching.

In yet other aspects of the invention, methods for classifying an object are provided. The methods include obtaining a set of variables associated with an object; ranking each of the variables according to their numerical value; and providing an human interface through which a user may interact.

In still other aspects of the invention, methods of classifying an unknown tissue are provided. The methods include measuring values of each variable of a set of variables for an index group of tissues and a contrast group of tissues, calculating mean value and differences of mean value for each variable of the set of variables from the index group of tissues and the contrast group of tissues, ranking the means and differences of the means between the index and the contrast groups, determining values of each variable in the set of variables in an unknown tissue, and comparing the measured values in the unknown tissue to rank orders selected from the group of ranked means of the index group, ranked means of the contrast group, and differences of the means between the index and the contrast groups.

In some embodiments, the methods also include displaying to a user a visual indication of a relationship described by the comparison of the measured values of variables in the unknown tissue and the rank orders of the index and contrast groups. Preferably the methods include coding display indicators, such as symbols or tones, based on the positive or negative values of the means and the differences of the means. In certain embodiments, the visual indication is a ternary plot. In preferred embodiments, the variables are genes and the values are levels of gene expression; more preferably, the values are expressed as log of gene expression.

According to still other aspects of the invention, computer-readable media are provided that are encoded with one ore more programs that, when executed on a computer system, perform one of more of the foregoing methods. Computer systems for implementing such methods also are provided in accordance with the invention.

These and other aspects of the invention will be understood with reference to the drawings and the detailed description below.

BRIEF DESCRIPTION OF THE DRAWINGS

FIGS. 4–6 depict plots of the same data analyzed in FIGS. 1–3, using an alternative rank order plot. In these plots, the rank order of the contrasting tissue expression is plotted on the Y (right) axis. As in FIGS. 1–3, the rank order of the index tissue expression is plotted on the X (bottom) axis, and the log transformed data of unknown (challenge) tissue gene expression is plotted on the Z (left) axis.

FIG. 7 shows a listing of the 100 genes which best distinguish AML and ALL, as selected by standard statistical approaches.

FIG. 8 depicts a listing of the 100 genes which best distinguish AML and ALL, and their rank orders in AML and ALL, along with expression values for each AML and ALL test tissue in additional columns.

DETAILED DESCRIPTION OF THE INVENTION

Figure 1:
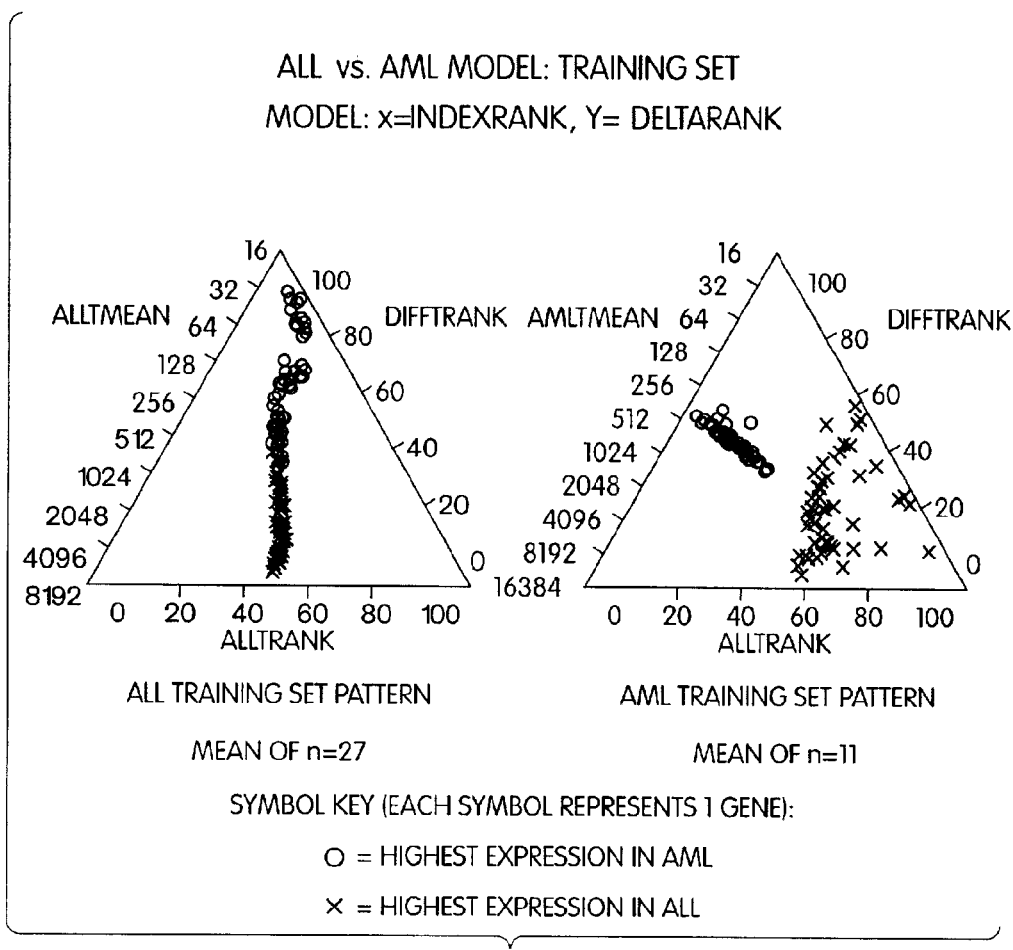
FIG. 1 depicts ternary display of the ALL vs. AML model defined by ALL(n=27) vs. AML(n=11) teaching sets. The model description is based upon plotting of Index tissue rank order (ALLTRANK) and Rank order of difference between Index and Contrasting Tissue (DIFFTRAN). Two plots are shown, one for each tumor type. When the ALL teaching set means (ALLTMEAN) are plotted on the third axis (left panel), a linear vertical array of datapoints results. When the AML teaching set means (AMLTMEAN) are plotted (right panel) on the third axis, the cloud of circles migrates to the left and cloud of crosses to the right. Notice also the number of symbols on the axes. Circles=genes expressed higher in AML; Crosses=genes expressed higher in ALL.

The invention described herein relates to the classification of objects of medical diagnostic relevance. The object can be a tissue, fluid or other bodily component, such as normal or cancerous tissues. The invention will be described primarily as it relates to tissues, although it will be understood that the invention is more broadly applicable to other bodily components and objects.

In certain embodiments of the invention, an initial evaluation is generated using a training set of objects. As used herein, a "training set" or "teaching set" is a group of objects, such as tissue samples, of known kind (e.g., phenotype). Preferably the tissues used for generating training sets are classified using standard methods such as histology and/or antibody recognition. The training set of objects is assayed for desired variables to establish patterns of data that serve to distinguish the training set of objects from a different kind of objects. In some embodiments, two representative objects of two distinct classes of objects are identified, although it generally will be preferred to assay a larger number of representative objects to establish variables characteristic for each type of object. For example, when examining tissue samples, multiple samples of known histological type are assayed for a plurality of variables.

Preferably, a large number of variables associated with the two classes of objects are measured, and a subset of these variables which best distinguishes the two objects is identified through one or more statistical processes. Collectively these variables describe the distinction between the two objects, preferably within a predetermined statistical confidence range. The subset of the variables can be used subsequently to classify unknown objects presumed to be a member of one of the two distinct classes.

The data acquired for the variables are transformed to a scaleless rank order. This transformation eliminates units of measurement, thus providing cross-platform comparability. For example, data generated for gene expression analysis of tissues by different manufacturer's fluorescent microarray readers can be directly compared following the data transformation, preferably following calibration using reference gene analysis. Thus training sets generated by a certain type of microarray reader can serve as comparative data for diagnosis of unknown tissues using expression data generated using a different type of microarray reader.

Examples of variables include: gene expression (e.g., data obtained via DNA microarray or protein microarray), tissue histology morphometry (nuclear size, chromatin texture index, percentage distribution of cell types), tissue or cell growth conditions and properties (in vitro culture nutritional requirements, cell division rate, etc.).

The robustness and utility of the model are attributable to several unique features including the following. First, incorporation of many variables permits accurate classification of objects based upon predominant trends between variables rather than reliance on one or a small number of variables. This "fuzzy" classification protocol is well suited to overlapping states (nonexclusive variable states for different objects) and rapid sensory (e.g., visual or auditory), rather than algorithmic, interpretation of data. Second, the ternary plotting system is refractory to linear scale changes. Once the model is constructed, the data entered from a test object is displayed in an identical fashion irrespective of multiplicative scaling of the variables. Third, the model used to define the display is extremely simple, based solely on rank ordering of quantitative index variables in two prototypical object states. It will be possible to translate the model between measurement platforms (from an Affymetrix expression system, for example, to a glass spotted microarray) by simple recalibration of variable rank orders in a series of calibrators. These calibrators could be a series of representative samples, or pooled specimens, measured in compared systems. Fourth, although the display described herein is configured for bimodal classification of objects with only two data states (e.g. normal tissue vs. tumor tissue, or tumor having good prognosis vs. tumor having bad prognosis), it could be expanded by performing a series of pairwise classifications, or increasing dimensionality (e.g., a three dimensional pyramid plot). Fifth, the output patterns are similar for a variety of models, thus achieving a degree of visual standardization for classification decisions irrespective of the tissues being studied. Sixth, incomplete test tissue data (e.g., missing values for some genes) has very little impact on classification performance when applied against a defined predictive model. Because the classification decision is based on displacement of a datapoint cloud, the reduced cloud density conferred by missing datapoints has no effect on the positions (and thus shifting) of the cloud itself.

The display of data clouds in a ternary (or other) plot permits the use of image recognition software to aid in classification. For example, a standard pattern (e.g., image) recognition software package can be linked to the data display to recognize or aid in the recognition of the tissue type being classified. The pattern recognition software can compare the data or image generated against training set data or images to differentiate between tissue types, or to suggest to the user a possible classification. The pattern recognition software can also be linked to a database containing standardized training set data or images of a variety of tissue types to facilitate the recognition of unknown tissue types. For example, if a tumor biopsy is isolated from a subject that does not present typical gross morphology or histology, a clinician may not be able to provide a suggestion as to classification of the tumor. In such cases, where the tumor biopsy is then screened by a methodology generating multivariate data, such as microarray gene expression profiling, the clinician or laboratory technician may not be able to select an appropriate group of training sets against which to compare the image or data generated by the method of the invention. In such cases, pattern recognition software linked to a database may be able to search for a data or image pattern from a database containing many training set patterns, thereby providing the clinician or laboratory technician with a classification or a small group of potential classifications from which the classification can be made.

In certain embodiments, software for performing the statistical manipulations described herein (transformation to scaleless data) can be provided on a computer connected by data link to a data generating device, such as a microarray reader. Any standard data link can be used, including serial or parallel cables, radio frequency or infrared telemetry links. Alternatively, data can be transferred by computer-readable medium (e.g., magnetic or optical medium) and read by the software. The data also can be entered directly by the user via user interface, such as a keyboard, monitor, etc. The computer may be contained within the data generating device, providing an integrated system for generating raw data, transforming the data to scaleless data, and displaying such data. One or more computers also may be linked to one or more data generating devices and one or more display devices, such as in a local area network or wide area network.

After acquiring the raw data from the data generating device, the data for the variables examined can be transformed to scaleless data (e.g., rank order data) in accordance with the methods of the invention. The software can allow the user to select a number of variables preferred for classification, or the software may provide scaleless data for a standardized set of variables (e.g., genes known to be useful for classification of a tissue type or set of tissue types). The software can execute data transformation algorithms from a preselected group, or can allow the user to input other algorithms. The transformed scaleless data can be stored in a data file, printed, and/or directly displayed to the user on a graphical user interface.

In one embodiment of the invention, a visual display is used to display the scaleless data for the classification of tissues. A ternary plot can be used as the visual display, provided to the user by a graphical user interface, such as a monitor, or a printer.

Other user interfaces known to one of ordinary skill in the art also can be used. For example, in other embodiments, an auditory display can be provided to the user to display the scaleless data for the classification of tissues. For these embodiments, the data for the variables is converted to distinct tones or series of tones. Thus a series of tones can be assigned according to an assignment scheme, with variable (e.g., a gene) representing a tone of a given pitch, to provide an acoustic scenario which may be easily recognized.

In one embodiment, the assignment of the series of tones is in rank order of expression within the training set index tissue and the series of tones is a progressive scale sequence. A different series of tones is assigned to the independently rank ordered contrasting tissue set, to yield a distinctly different melody or sequence. An unknown tissue then is assigned a series of tones based on the rank order of variable expressions in the unknown tissue. In another embodiment, the series of tones for the index tissue and/or contrasting tissue gene expression data is a non-scalar melodic pattern.

Other modifications to the tones may be made to differentiate the data of different sets. For example, certain auditory qualities can be modified, such as producing tones of different duration and/or intensity based upon a measure of proximity of rank order between the unknown tissue and the index tissue. Similarly, duration and/or intensity of tones can be varied based on the proximity of rank order between the unknown tissue and the contrasting training tissue.

The user can compare the tones generated by the software for the tissue being classified with training set tissues to determine the classification of the tissue. The user can select a best match between the unknown tissue and one of the acoustic signatures (tonal patterns) for the index and contrasting tissue classes. Other displays also may be used, including multimedia displays combining visual and auditory outputs described above.

EXAMPLES

As a proof of concept, gene expression in tissues of Acute Lymphocytic Leukemia (ALL) and Acute Myelogenous Leukemia (AML) were classified. The gene expression data show that the two tumor types have systematic differences in gene expression. The data published by Golub et al. (*Science* 286:531–537, 1999) were used; expression of 5000+ genes was analyzed from 27 (ALL) and 11 (AML) training tissues.

The 100 genes which best distinguish the two groups were selected by standard statistical approaches (FIG. 7). First, the mean expression values of the two groups were compared, and only those with a minimum-3-fold and 100-unit difference between means were retained. The logged means were then rank ordered by t-test and the top 50 genes which were upregulated in AML, and the top 50 upregulated in ALL were selected for modeling. This represented 100 genes, or variables, which distinguish the two groups of AML and ALL. The objective was to develop a model of how these variables can distinguish the object types, or tissue groups, and apply that model to classify new, or test, tissues.

The model was built using the mean values for each gene in the two tissues, and is completely described by only two variables: 1) the rank order of gene expression in the Index Tissue (TRANK), and 2) the rank order of the difference in expression (DIFFTRAN) between the two tissues (Index and Contrasting Tissue).

First, one of the two tissues was selected to be the Index tissue. The 100 variables in the index tissue were rank ordered by the mean expression of each to generate an Index Rank. The ALL training set was used to calculate an Index Rank for 100 genes in ALL. This was simply the rank order of genes sorted by their average expression amongst the 27 training ALL tissues. Rank ordering stripped away all absolute scale information.

Second, the Contrasting Tissue (AML) was compared to the Index Tissue (ALL), again using the mean expression for each gene. The genes rank were ordered by the difference between the means (Contrasting Tissue mean–Index Tissue mean; or AML–ALL). This supplied a scaleless rank-order distance metric between the genes called the DIFFTRAN.

Ternary Display of the Model

The next step in the classification analysis was to use the model, composed entirely of two values (TRANK and DIFFTRAN) for each of 100 genes, to classify a test tissue for which the 100 gene measurements were available.

Ternary, or triangular, coordinate displays were used to plot the two-dimensional model (dimensions 1 and 2, TRANK and DIFFRANK) against the test, or unknown tissue (dimension 3). Ternary displays permit plotting of three variables, each on a separate axis, in only two dimensions. This is possible when the three variables are known to have a fixed relationship, such as when they always add to the same number.

Ternary Plots are suited to binary object classification when the model is defined by variables with a fixed relationship to each other. In general, the following relationships hold true in the model:

Test Case=TRANK+DIFFTRAN.

If the test case was a member of the index group, then DIFFTRAN=0, and Test Case=TRANK. If the test case was a member of the Contrasting Tissue Group then:

Test Case expression−DIFFTRAN=TRANK

Thus, in cases where DIFFTRAN is not equal to zero (FIG. 1, Right, the plot axis rotates perpendicular to the axis when DIFFTRAN=0 (FIG. 1, Left).

Figures 1, 2A:
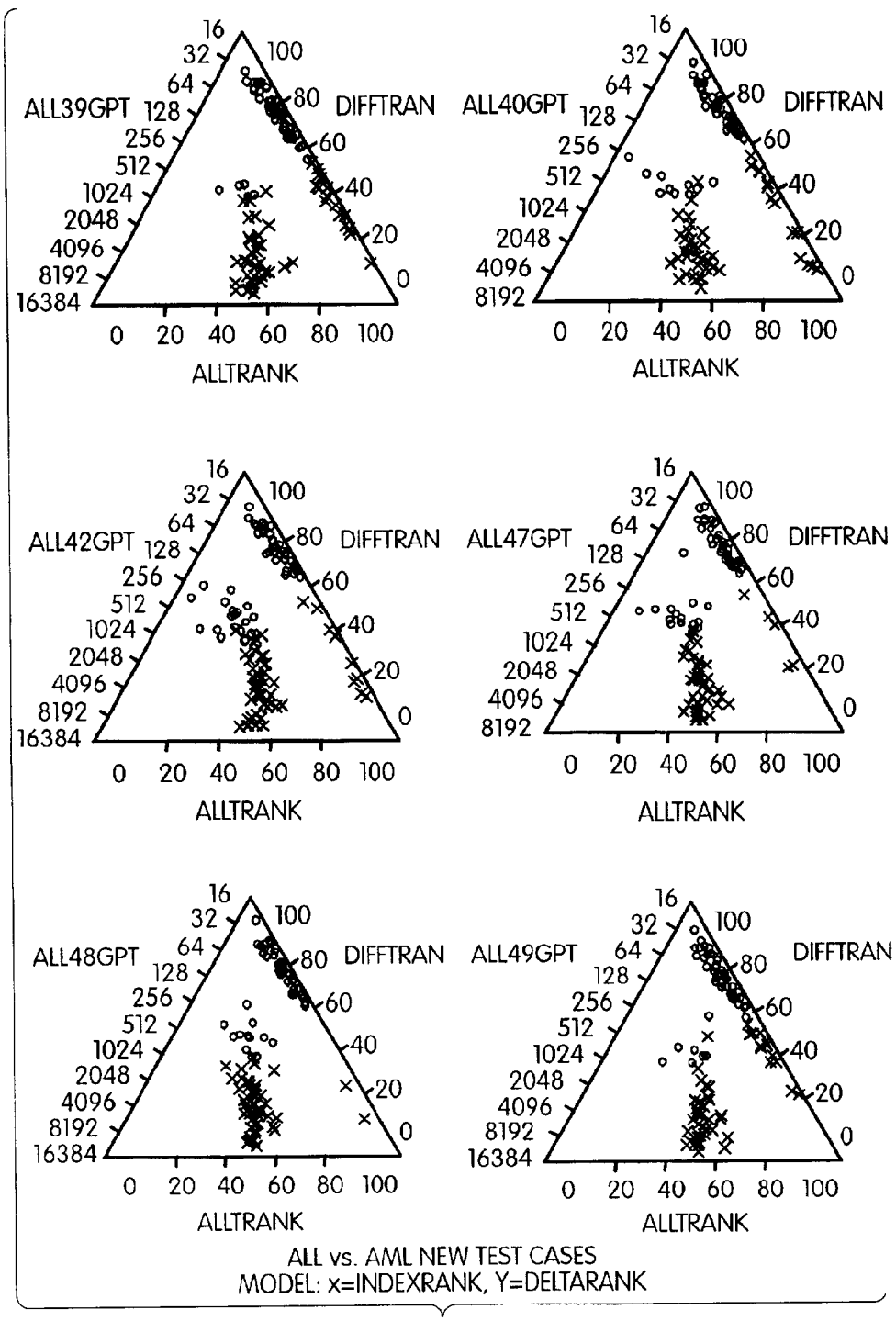
Figures 2, 2A:
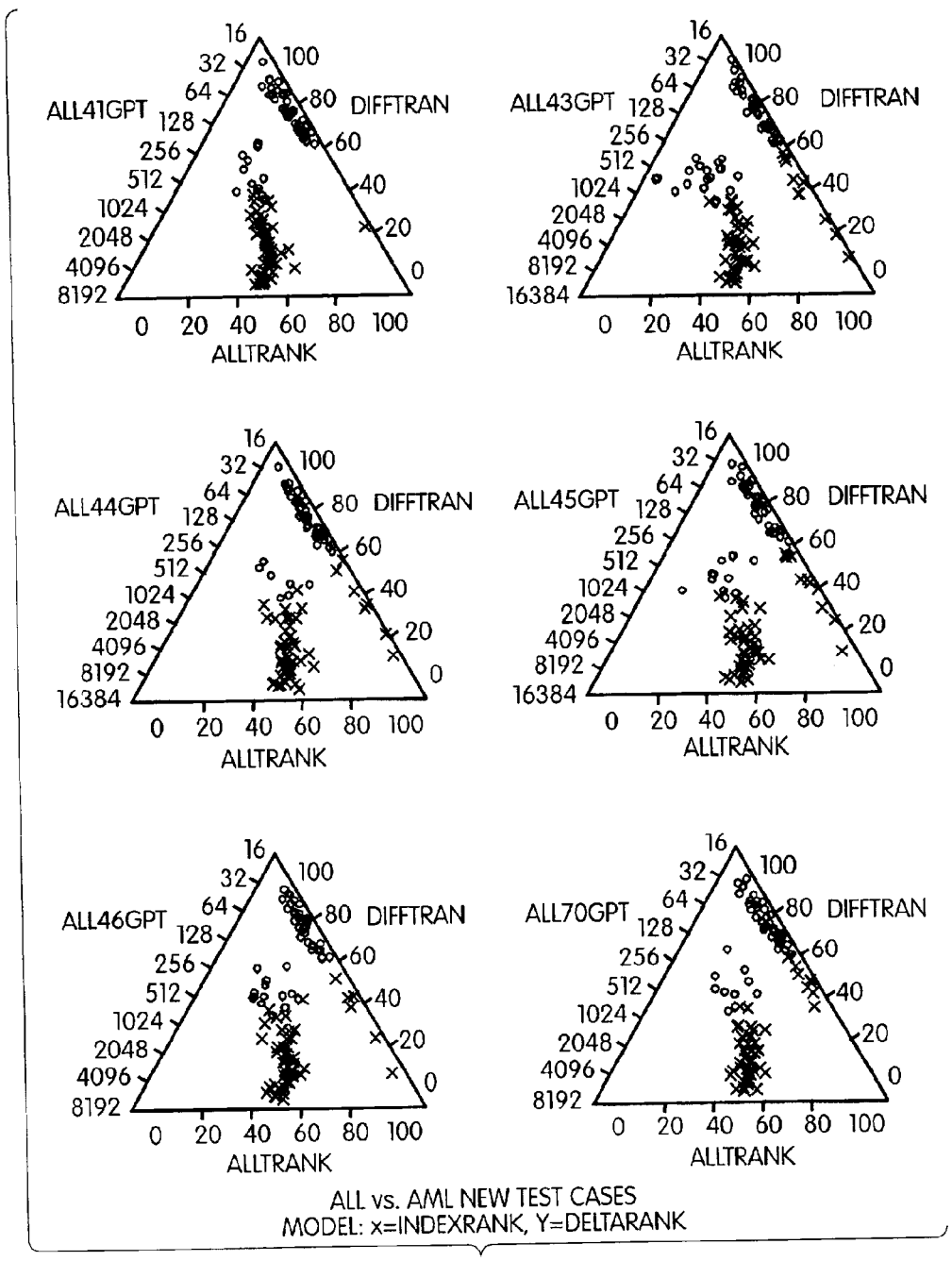
FIG. 2 depicts a challenge of the ALL vs. AML model with new test cases. Ternary plots of the model defined in FIG. 1 (right and bottom axes) were plotted against 20 new ALL (top) and 14 new AML (bottom) tissues. Note in the ALL tissues most circle symbols are in the vertical midline or on the right axis. In the AML tissues, the circle symbols tend to move away from the right axis, and veer to the left of midline. In the ALL tissues very few of the cross symbols are on the right axis—most are in the midline. In the AML tissues these move to the right and begin collecting on the right axis.

Using the Model for Prediction: Ternary Plot of Unknown Tissue Against Classification Model The ALL vs AML Model defined in FIG. 7 was used to generate a model template against which new test tissues could be displayed. A simple spreadsheet in which 100 rows each represent one gene define the model in two columns containing ALLTRANK and DIFFTRAN. Symbol color for each of the 100 genes was defined by the training set as red or blue, based upon direction of change between groups ("red" indicating genes expressed higher in AML; "blue" indicating genes expressed higher in ALL; these were graphed as circles and crosses, respectively, to show the differentiation in black and white figures). Expression values for each test tissue appear in additional columns (FIG. 8). FIG. 2 shows the data cloud patterns in ternary plots as predicted for ALL (top) and AML (bottom) test tissues, and should be compared to the training set shown in FIG. 1. ALLTRANK (bottom axis) and DIFFTRAN (right axis) rank order values for each of 100 genes were calculated from a training set of 27+11 tissues, and plotted against the test tissue expression value (Left Axis) for each of the 100 genes. These plots were generated using an actual dataset, in which FIG. 2 test tissues had no input into defining the model (training sets).

The axes for FIG. 2 shows AML and ALL test cases. Bottom Axis: TRANK=Rank order of expression level in Index Tissue. Right Axis: DIFFTRAN=Rank order of difference between Index and Contrasting Tissue. Left Axis: Log of expression in Unknown Tissue. Symbol shape was used to show direction of difference in model, although other variations of the data cloud (e.g., color of data points) would work equally well.

When the AML teaching set means (AMLTMEAN) are plotted (Right) on the third axis, the circle symbol cloud migrates to the left and cross symbol cloud to the right. Visibility of the axis associated datapoints (symbols on the axes) can be improved by slight jittering, to reduce overlap. The differences in the data clouds in these ternary plots permit ready differentiation of ALL from AML tumors by just glancing at the plots.

Figures 2, 2A, 3:
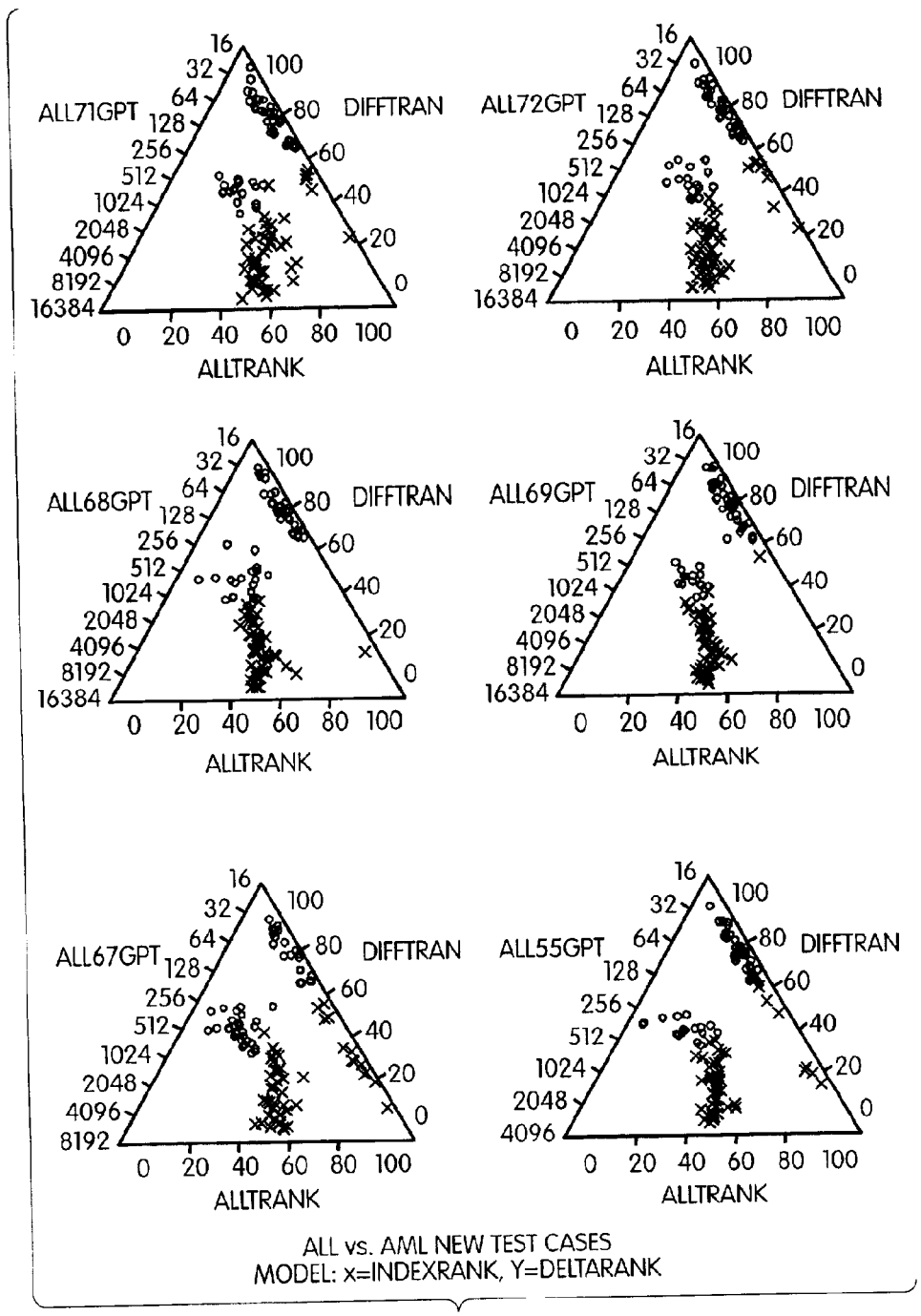
FIG. 3 depicts ternary display of two breast cancer types. 100 genes which distinguish two types of breast cancer (designated H and L) were used to develop a model (upper row). Individual tissues of known classification which were part of the training set are shown below. Note data cloud shifts in individual tissues reflect trends summarized in the model.

FIG. 3 shows comparable ternary displays for an entirely different tumor type, breast cancer, emphasizing that the display appearance is maintained independent of the genes selected, or tumor type studied. The individual cases shown in FIG. 3 (all but the top row) are the actual training cases used to generate the model shown in the top row. In this case, the individual patterns reproduce the trends seen in the average model.

Figures 2, 2A, 3, 4:
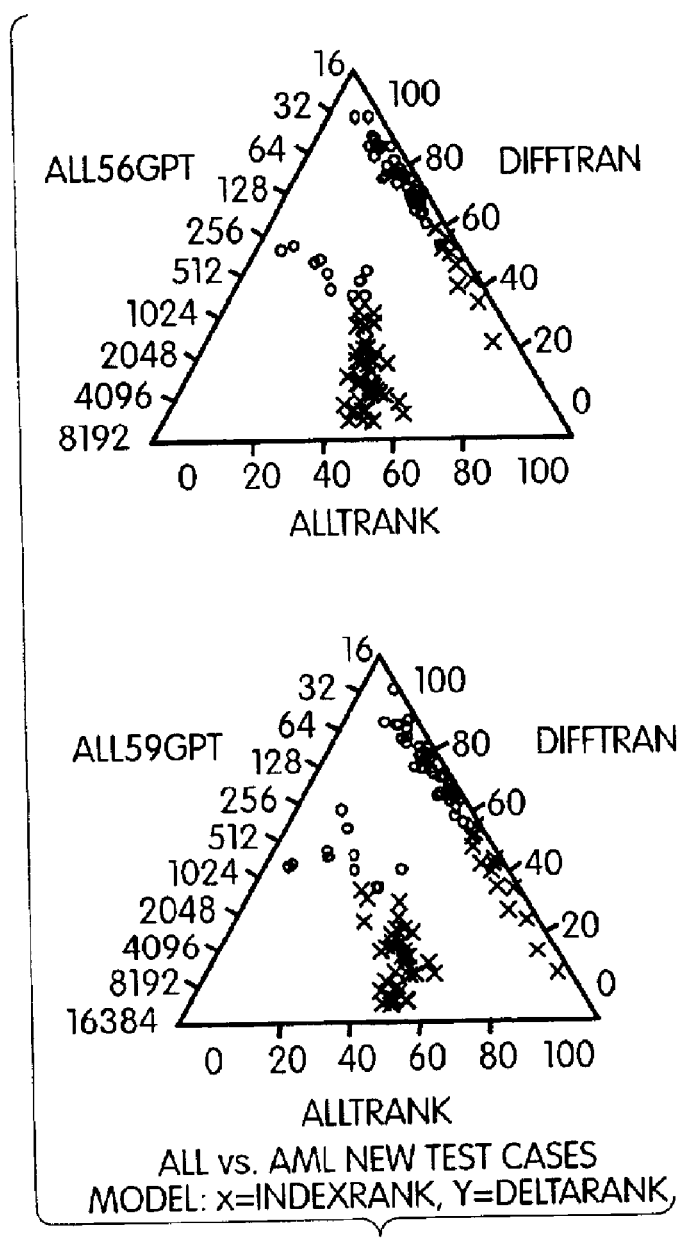
Figures 1, 2B:
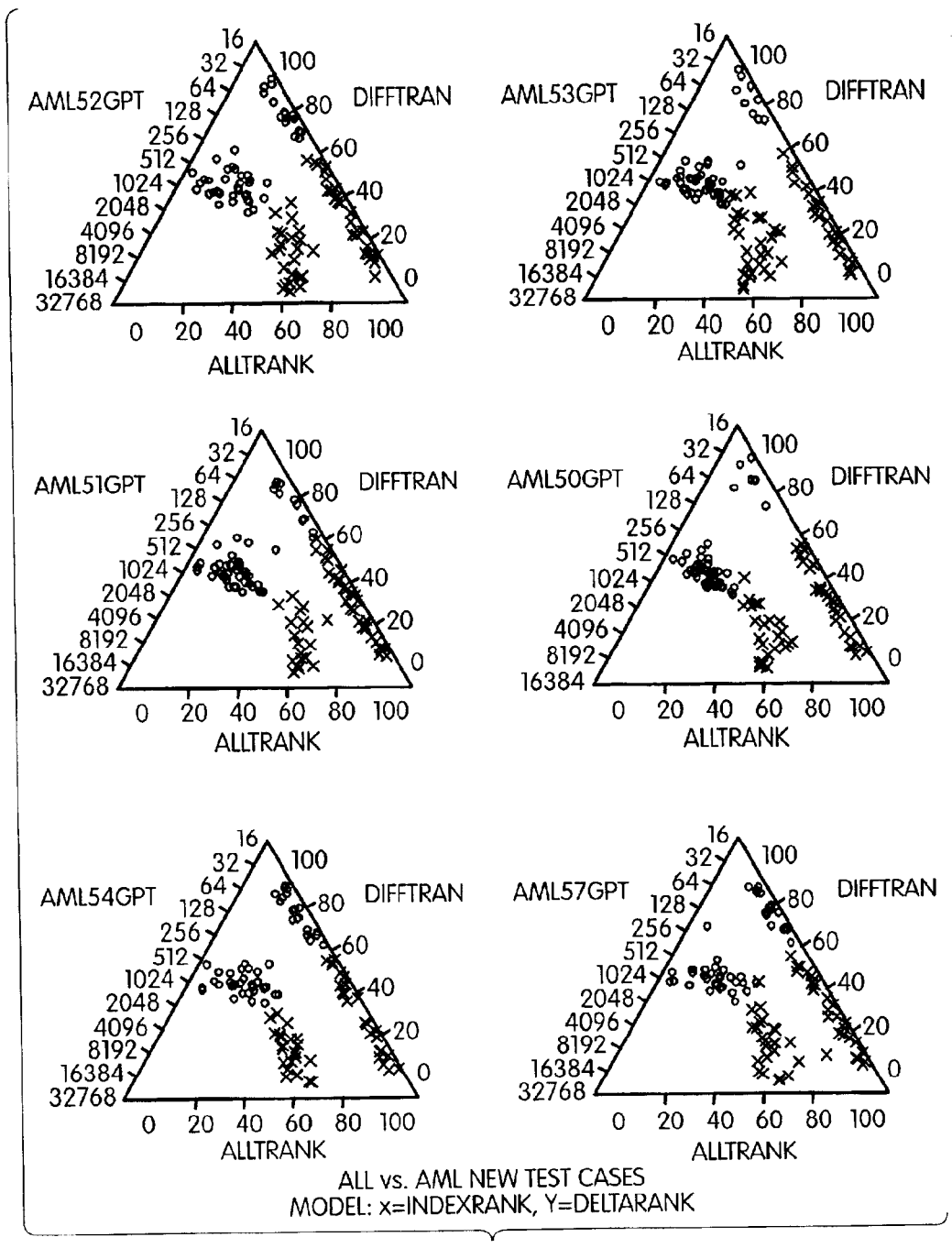
Figures 2, 2B:
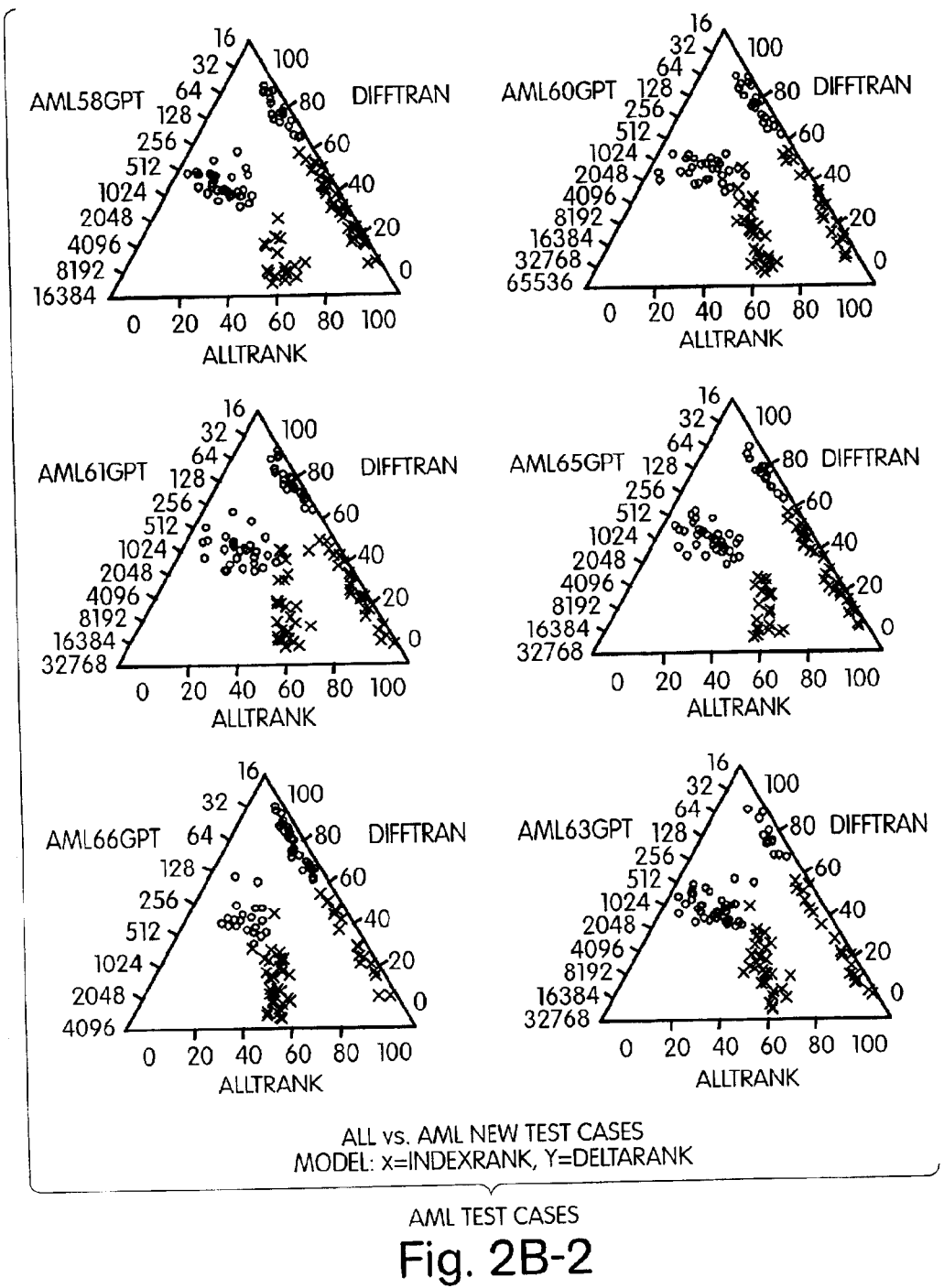
Figures 2, 2B, 3:
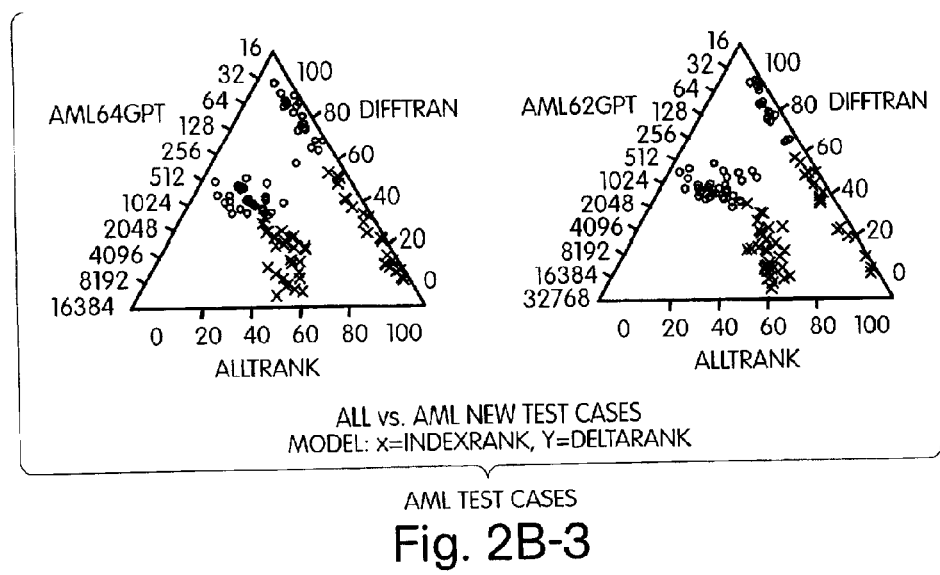
Figure 3A:
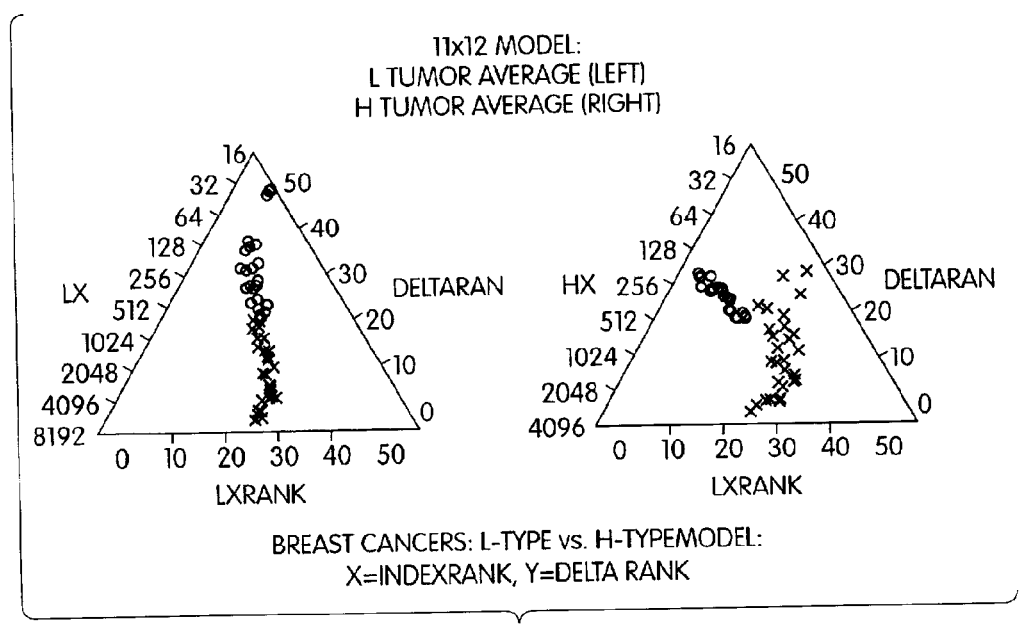
Figures 1, 3B:
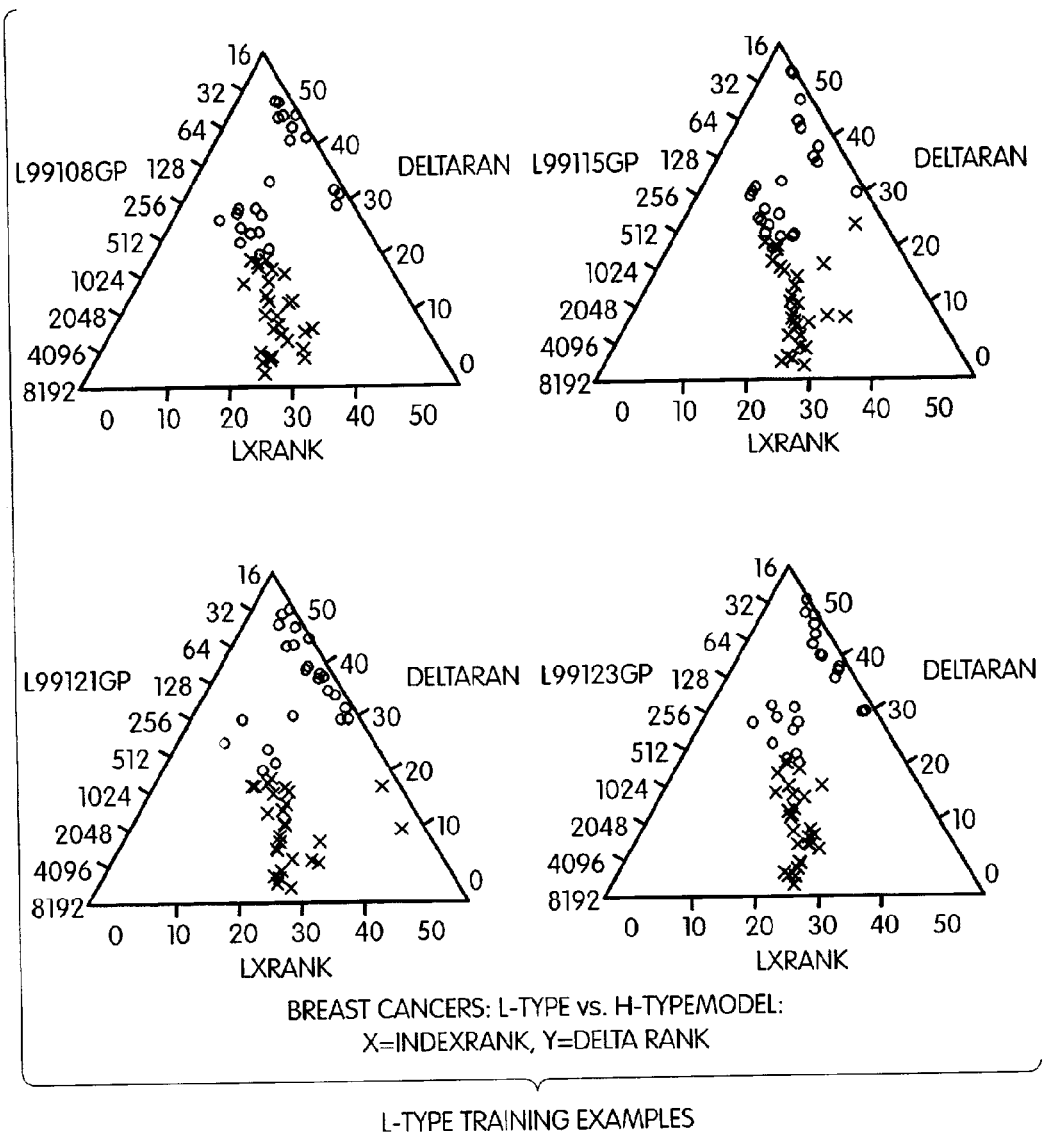
Figures 2, 3B:
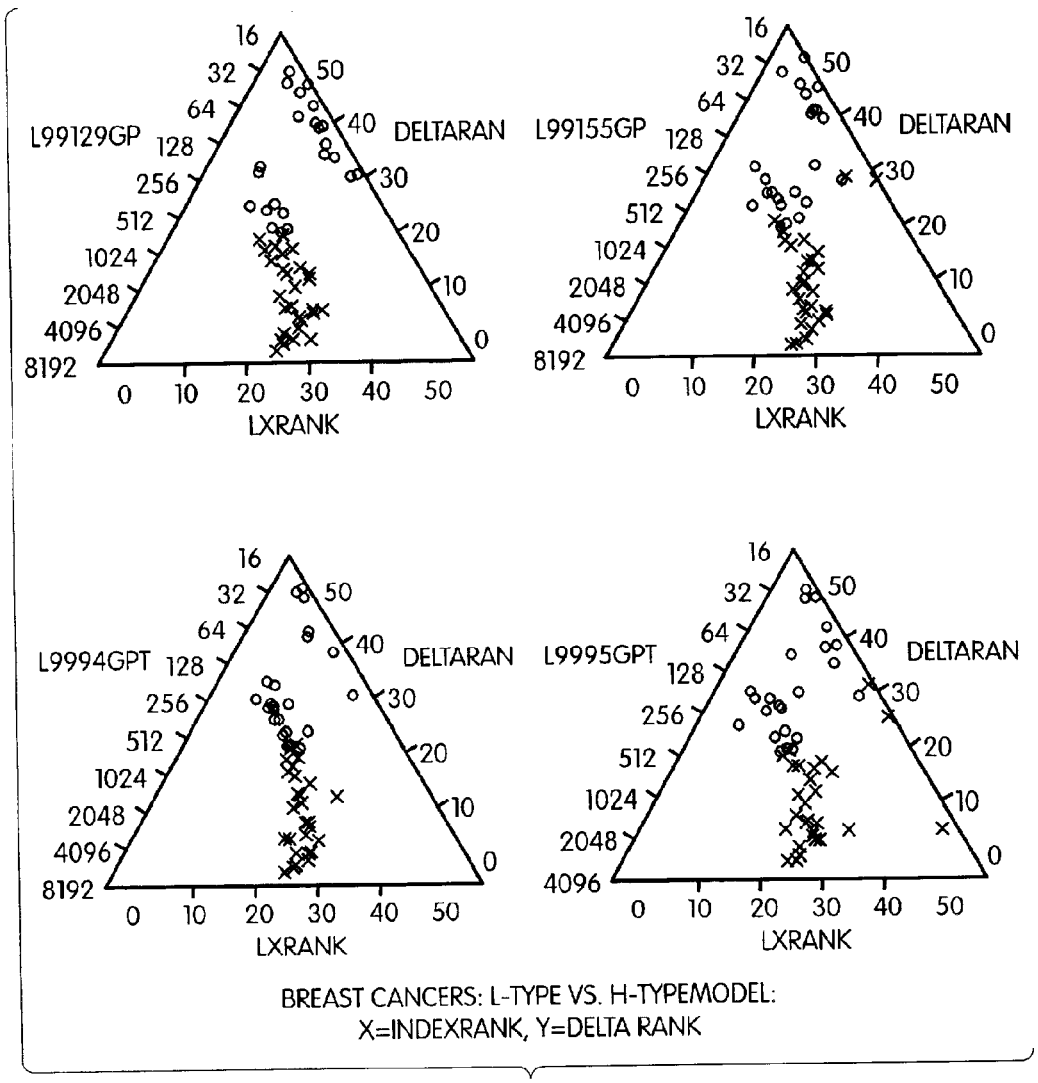
Figures 1, 3C:
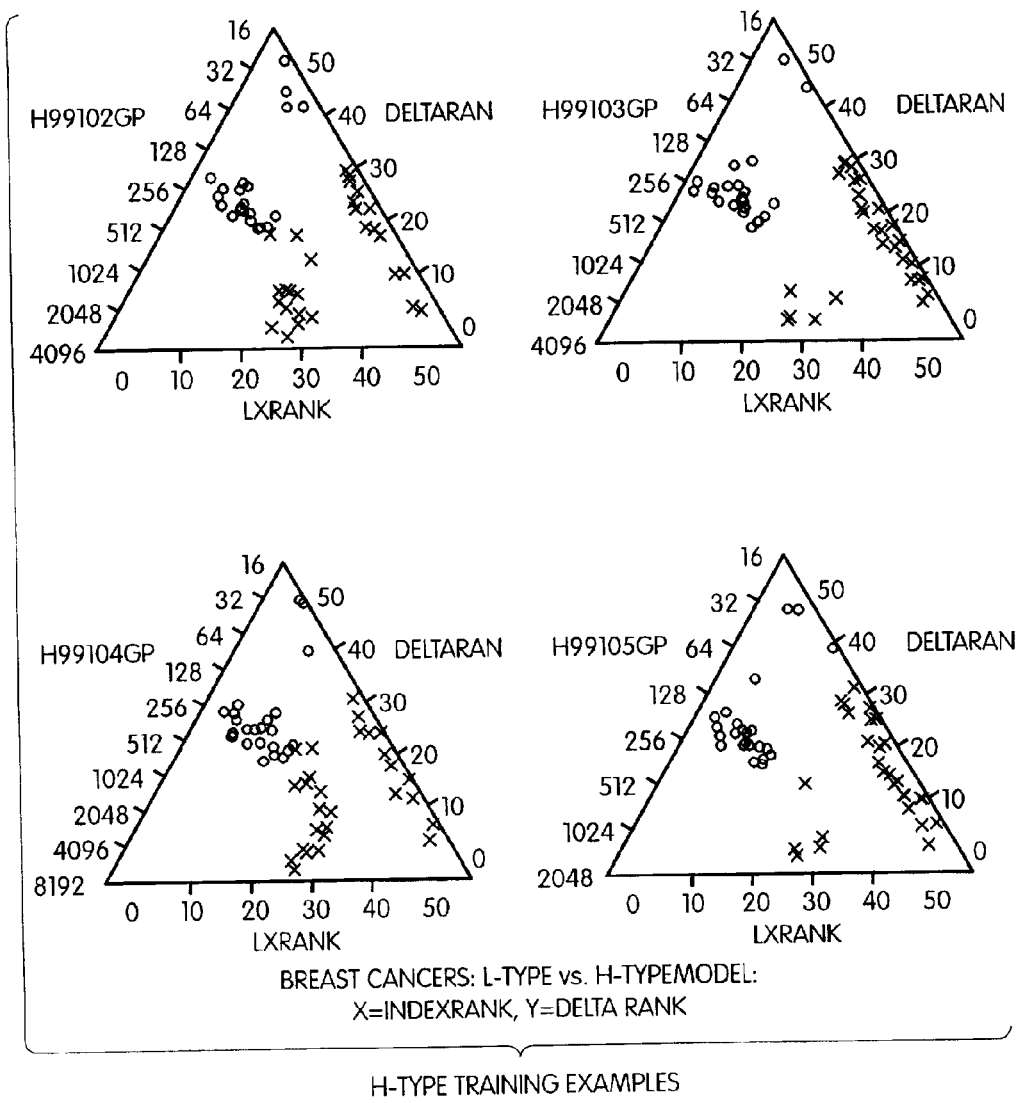
Figures 2, 3C:
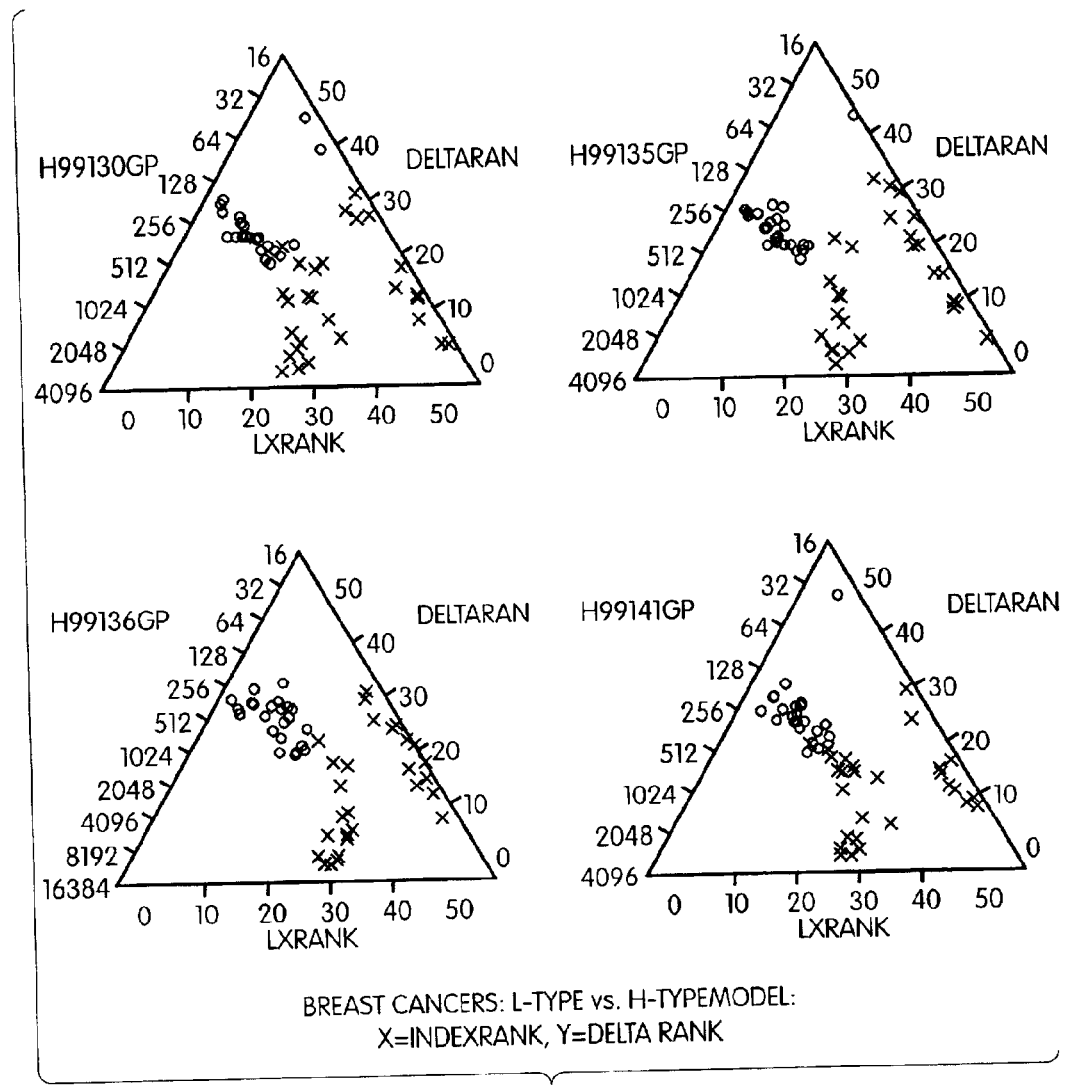
Figure 4:
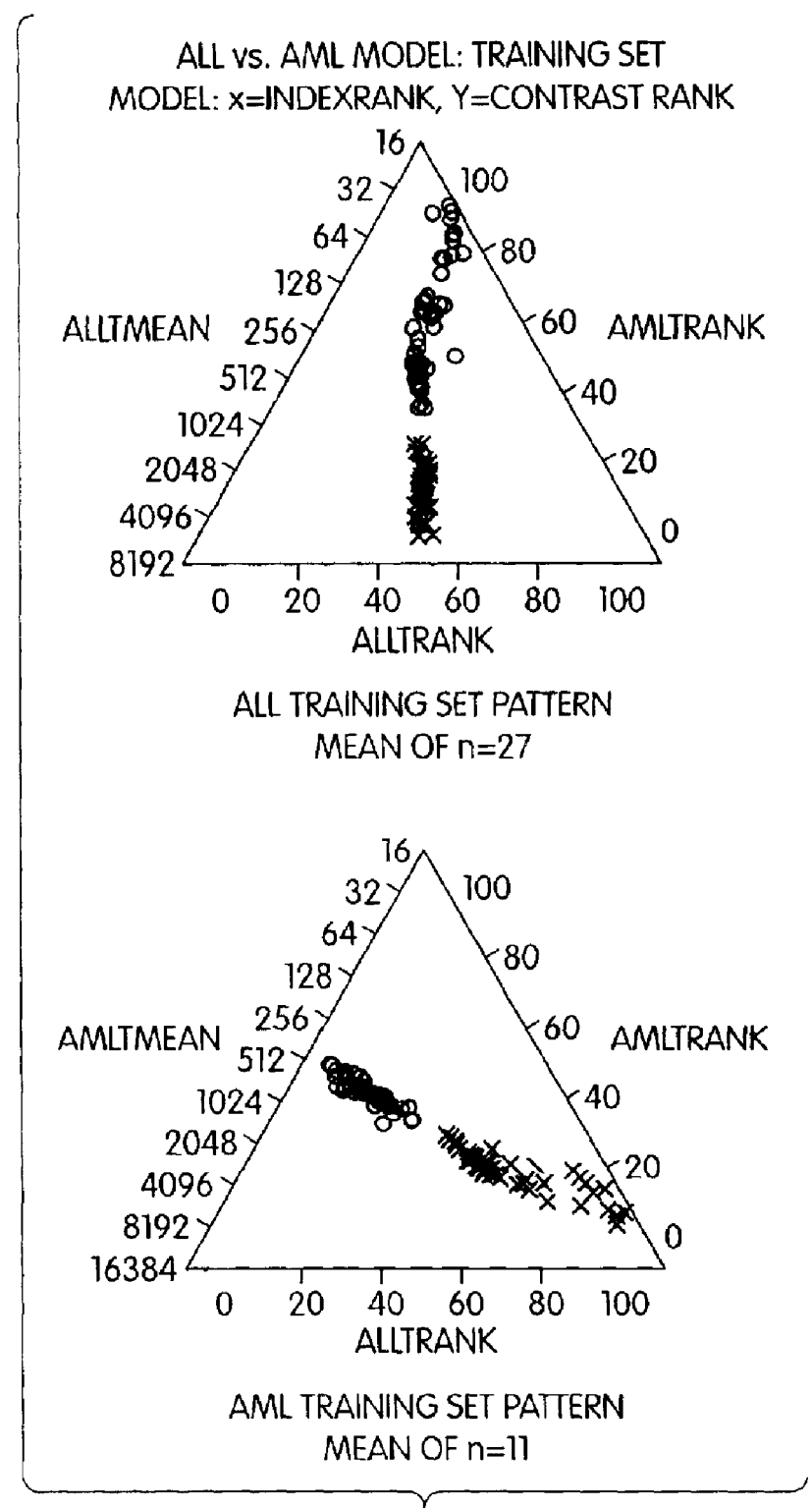
Figures 1, 5A:
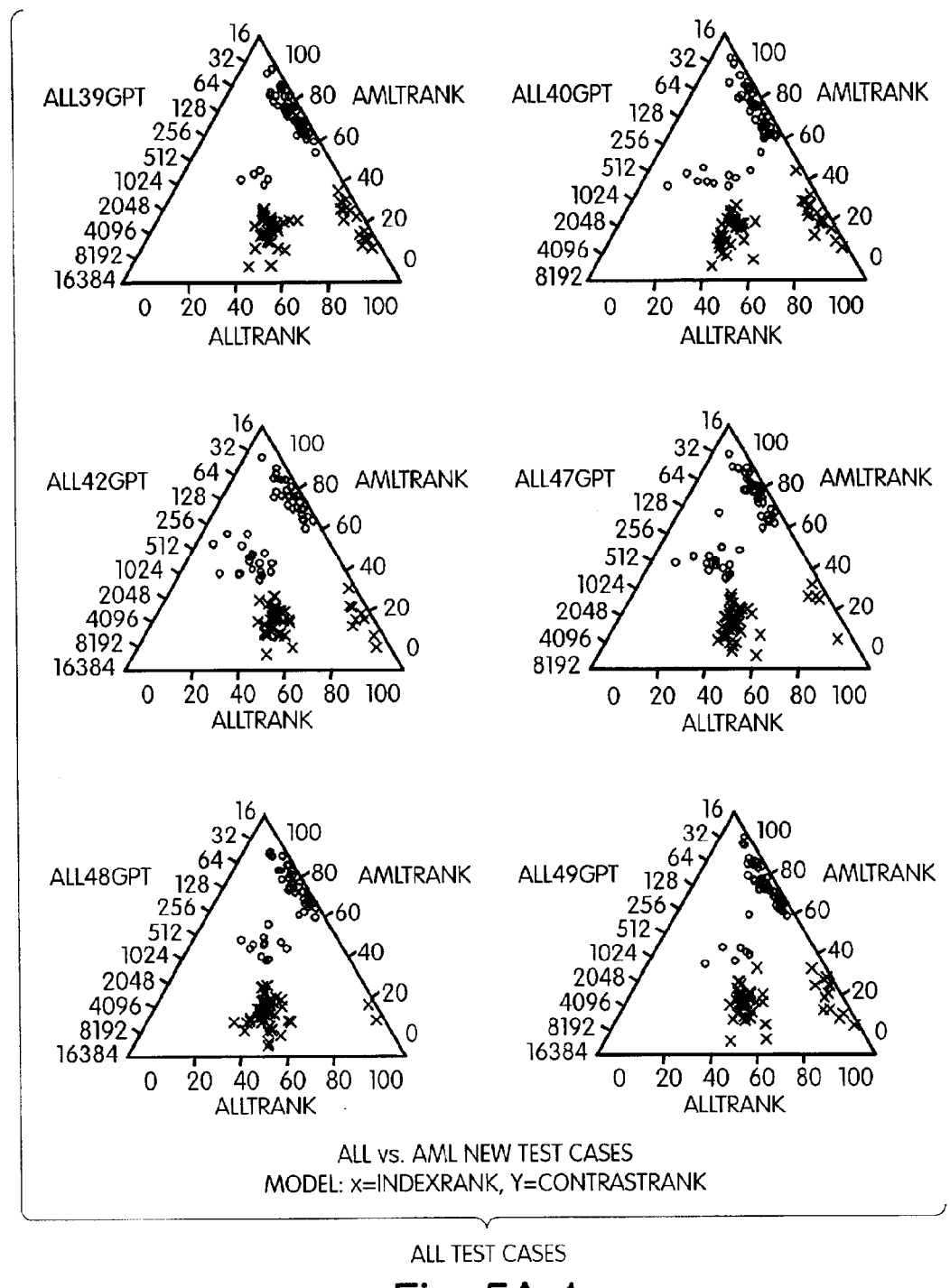
Figures 2, 5A:
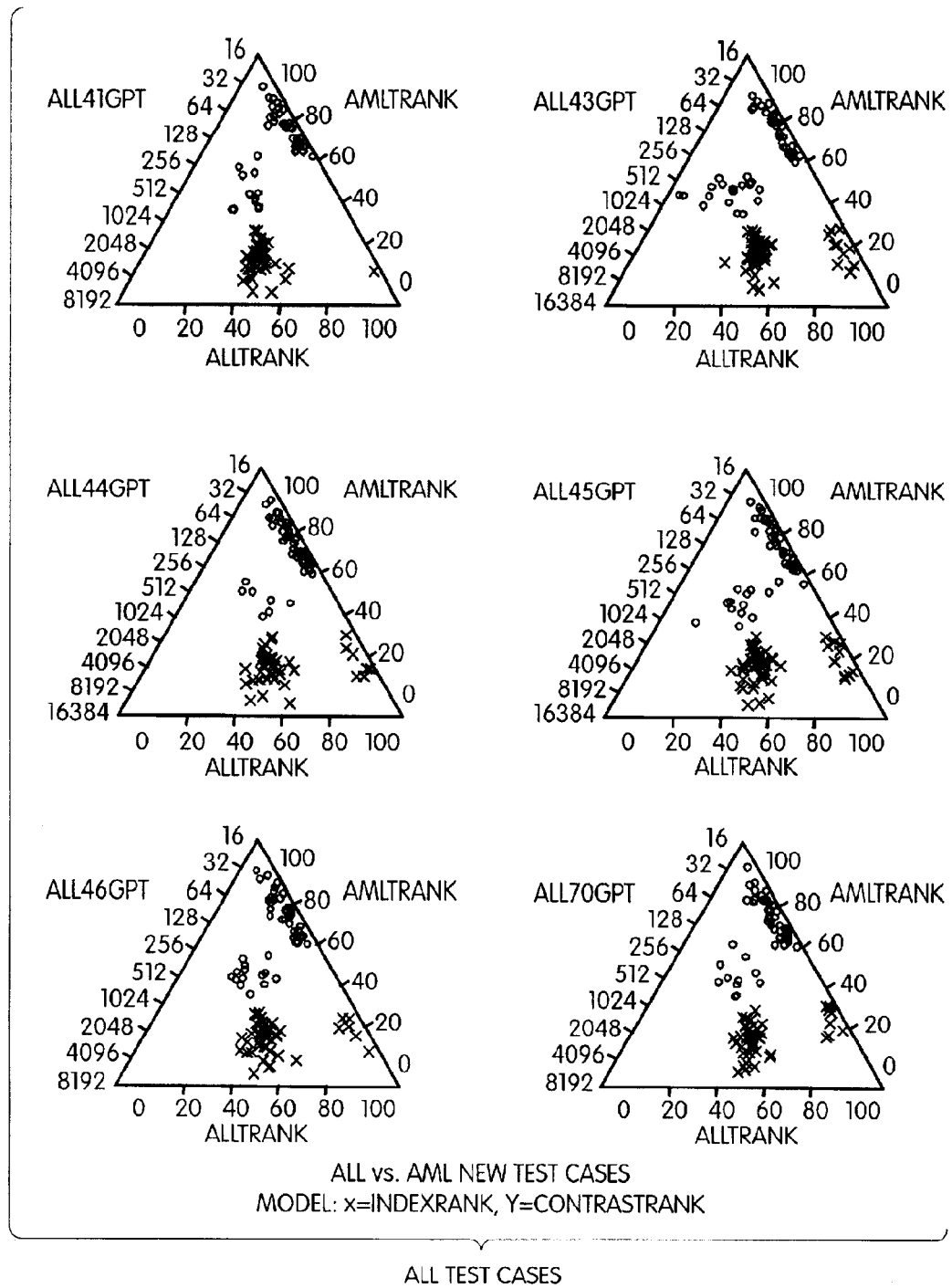
Figures 3, 5A:
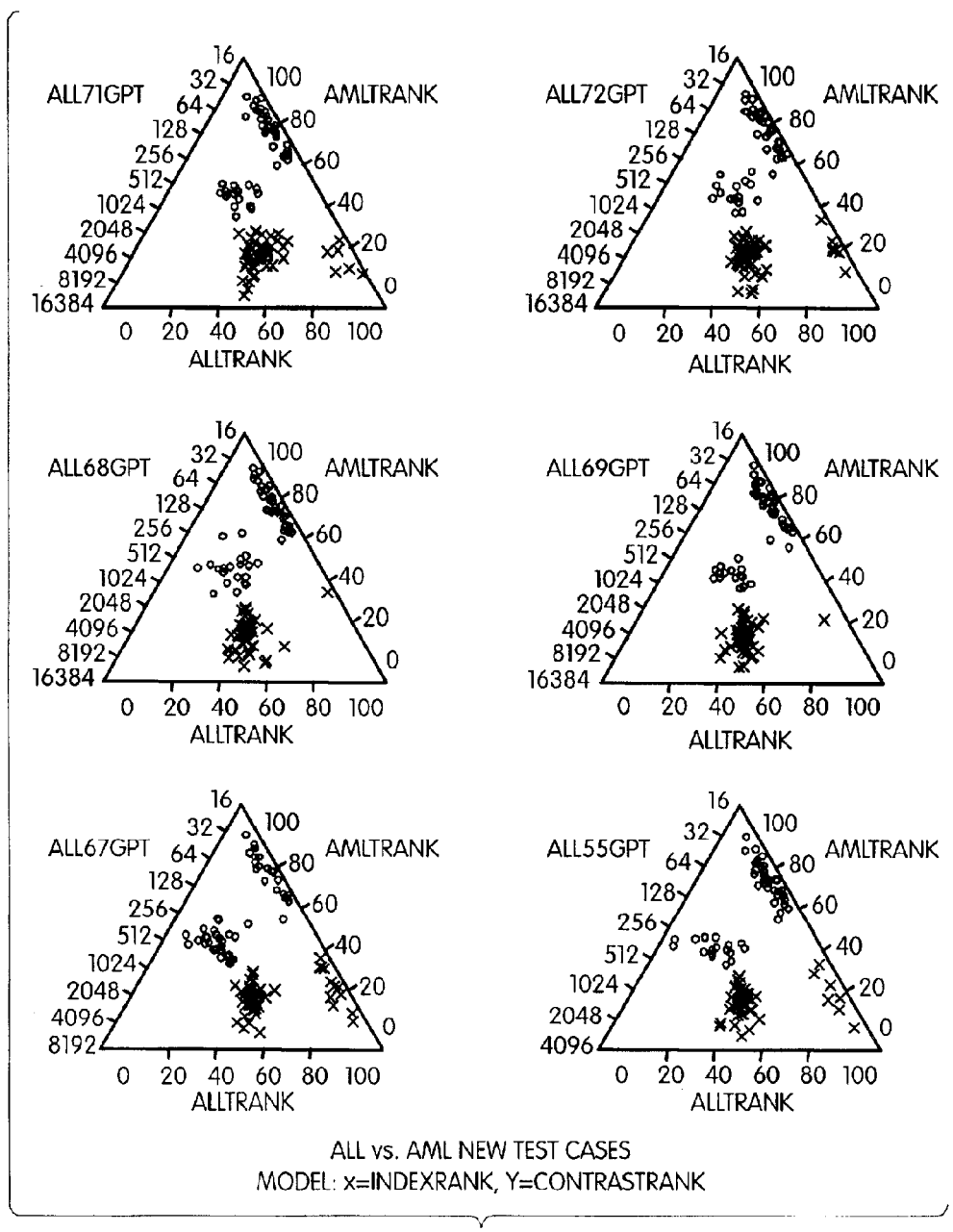
Figures 4, 5A:
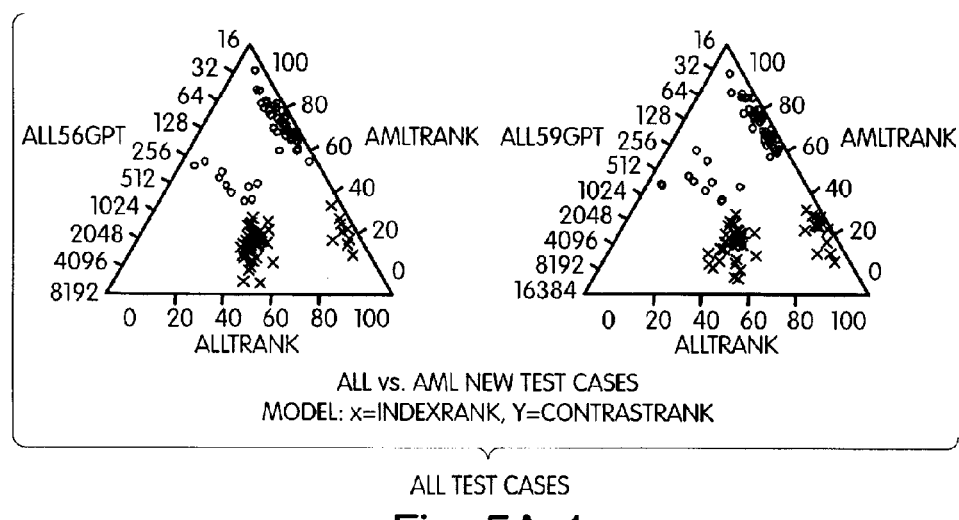
Figures 1, 5B:
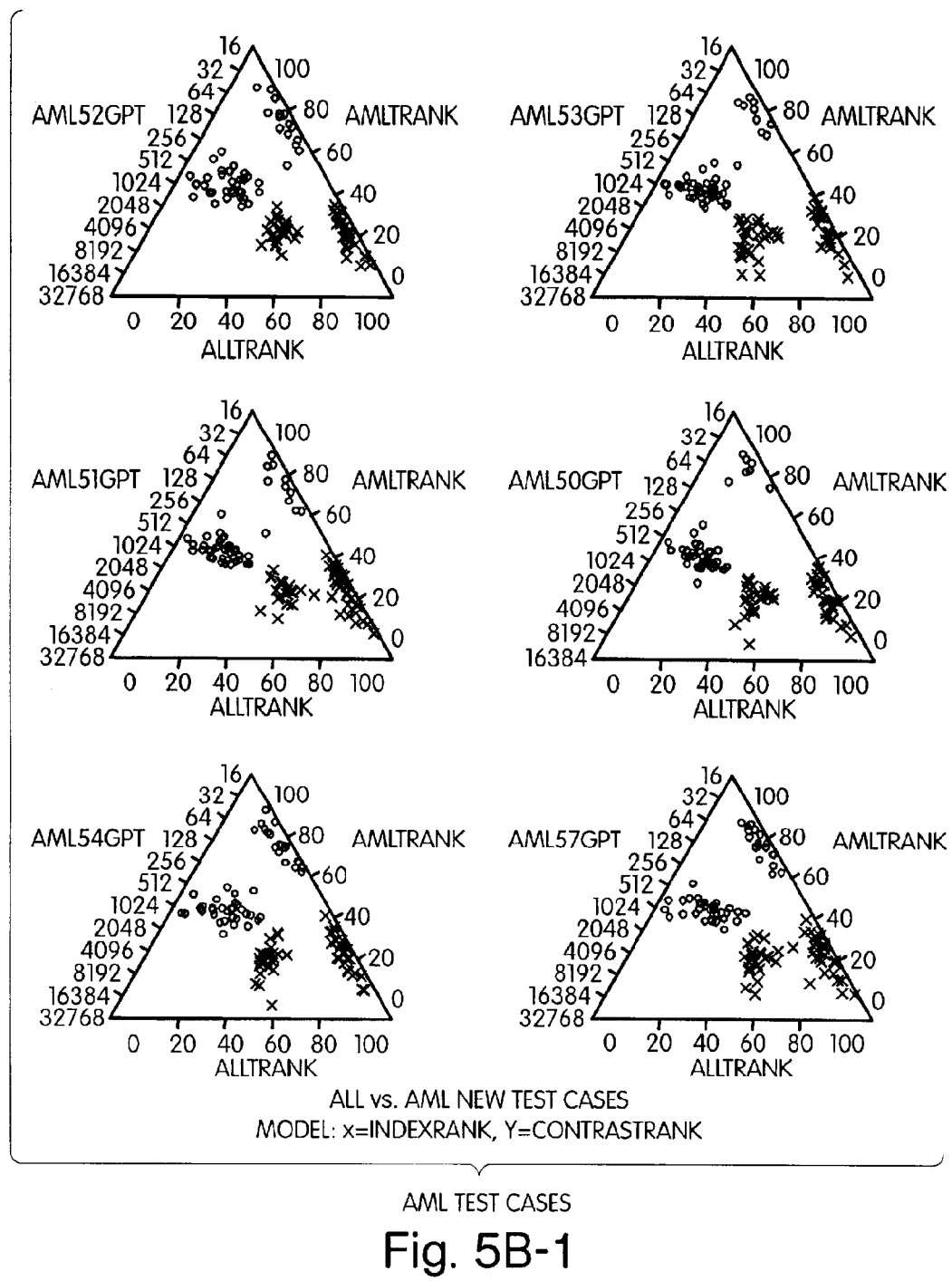
Figures 2, 5B:
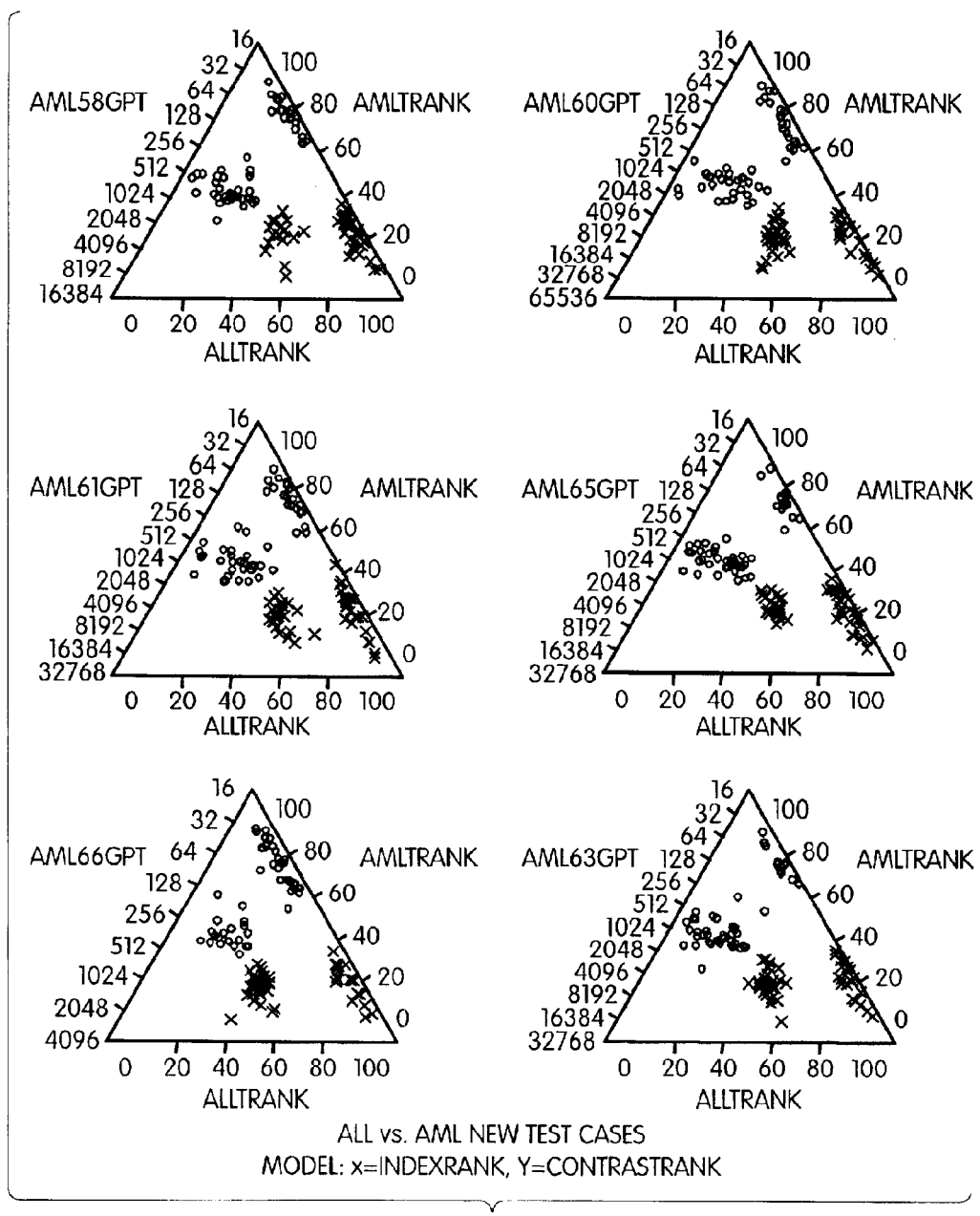
Figures 3, 5B:
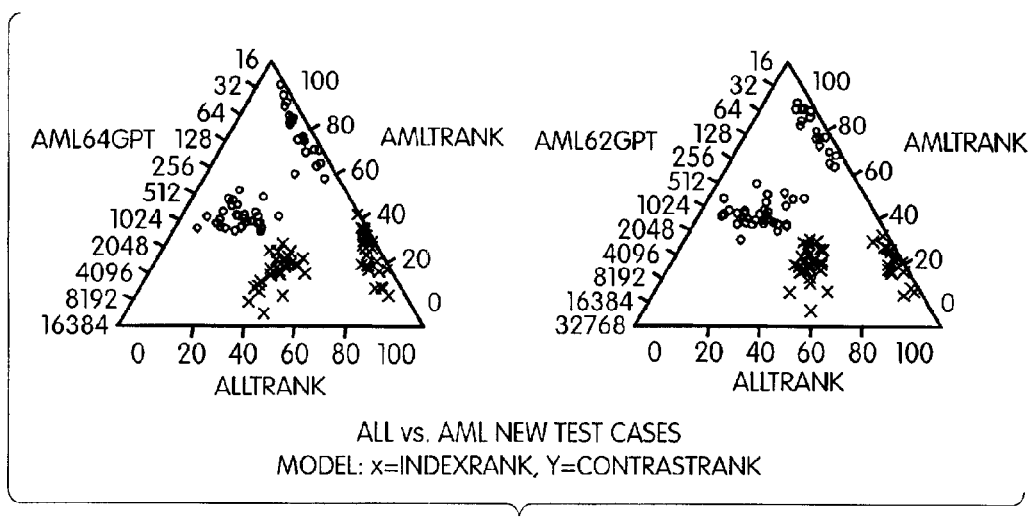
Figure 6A:
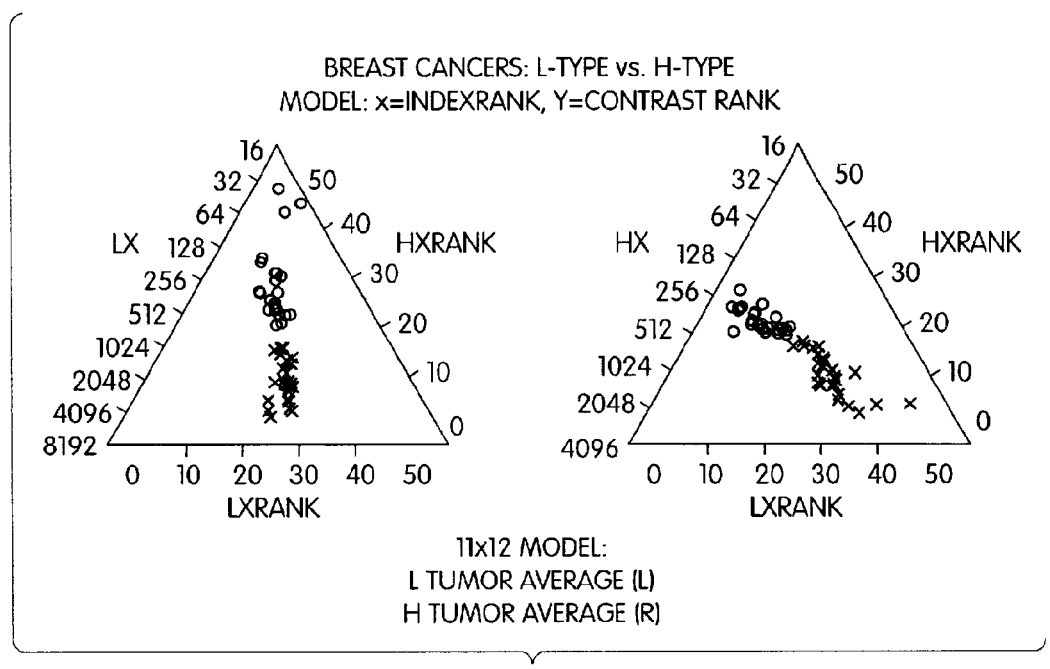
Figures 1, 6B:
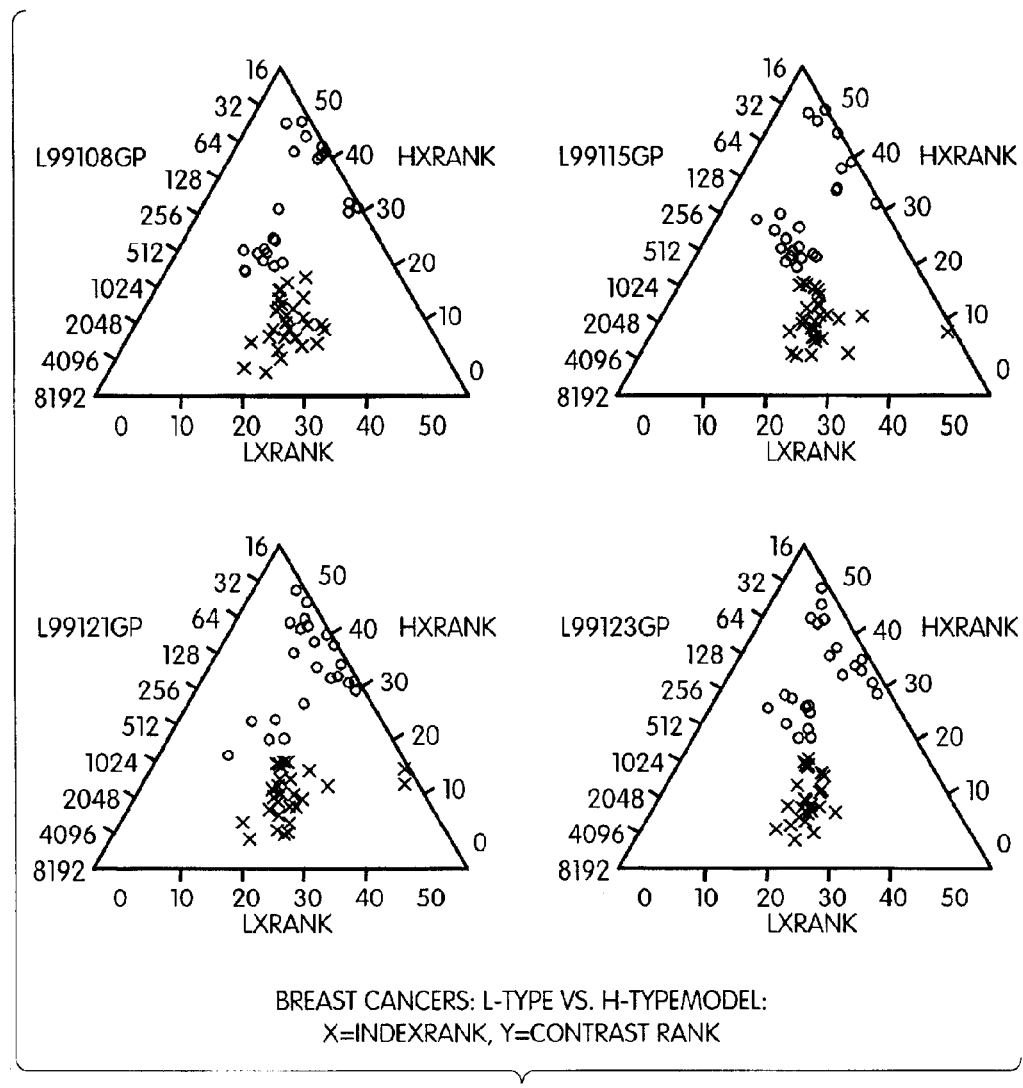
Figures 2, 6B:
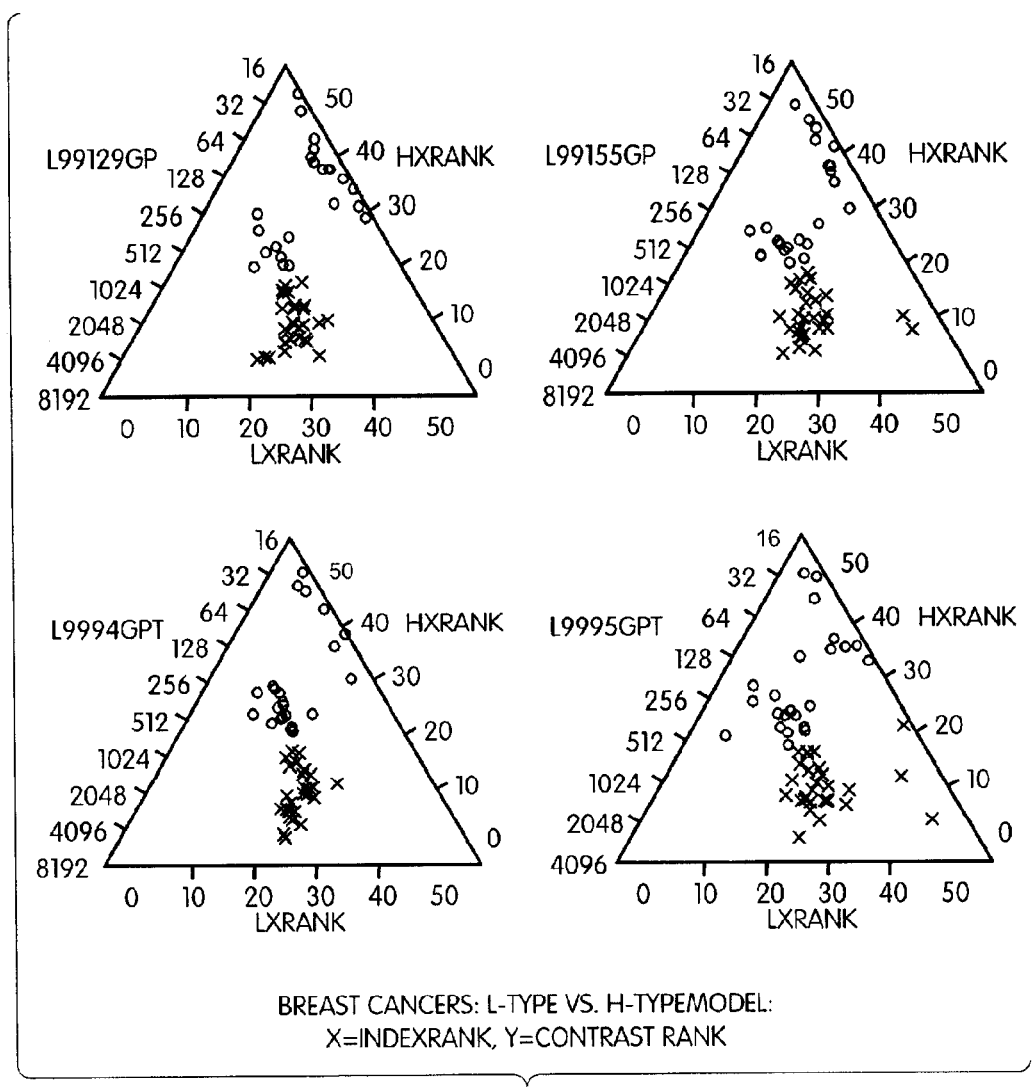
Figures 1, 6C:
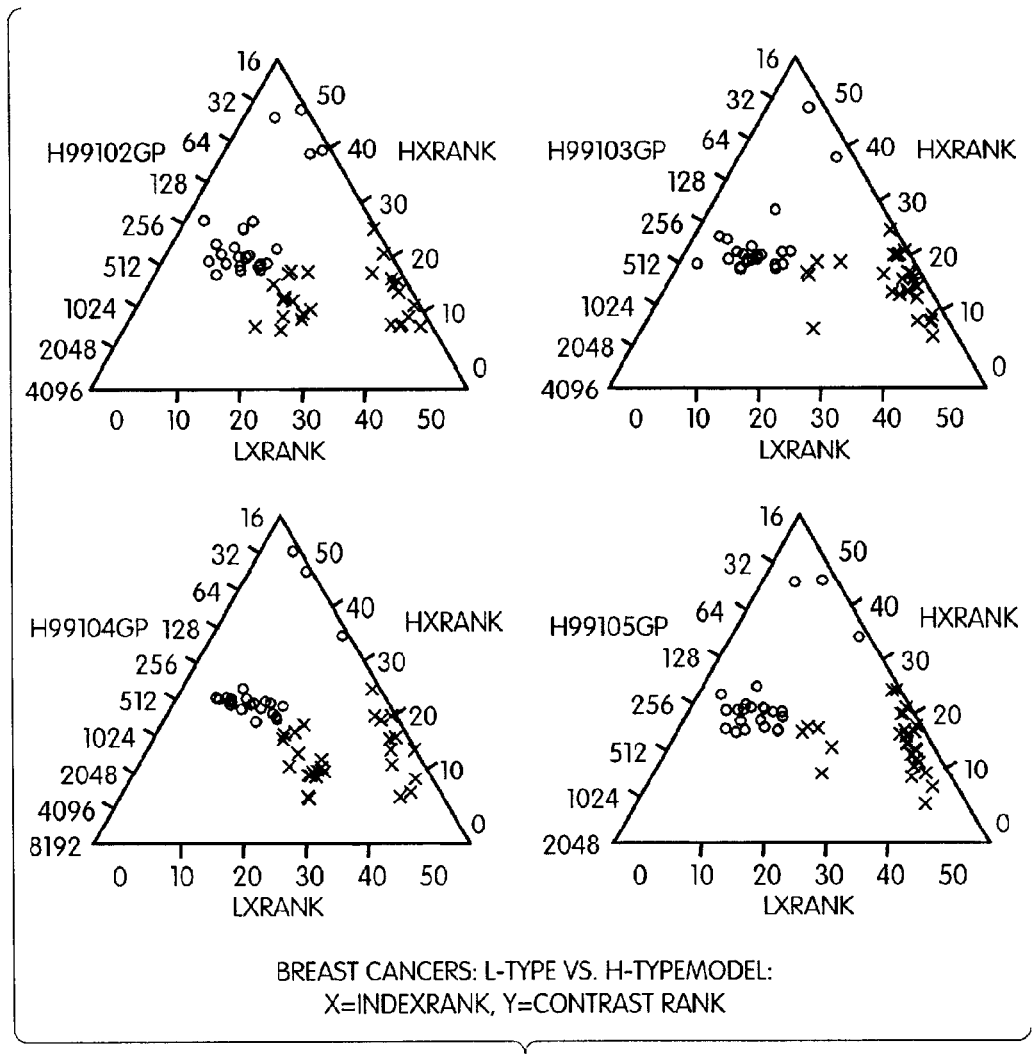
Figures 2, 6C:
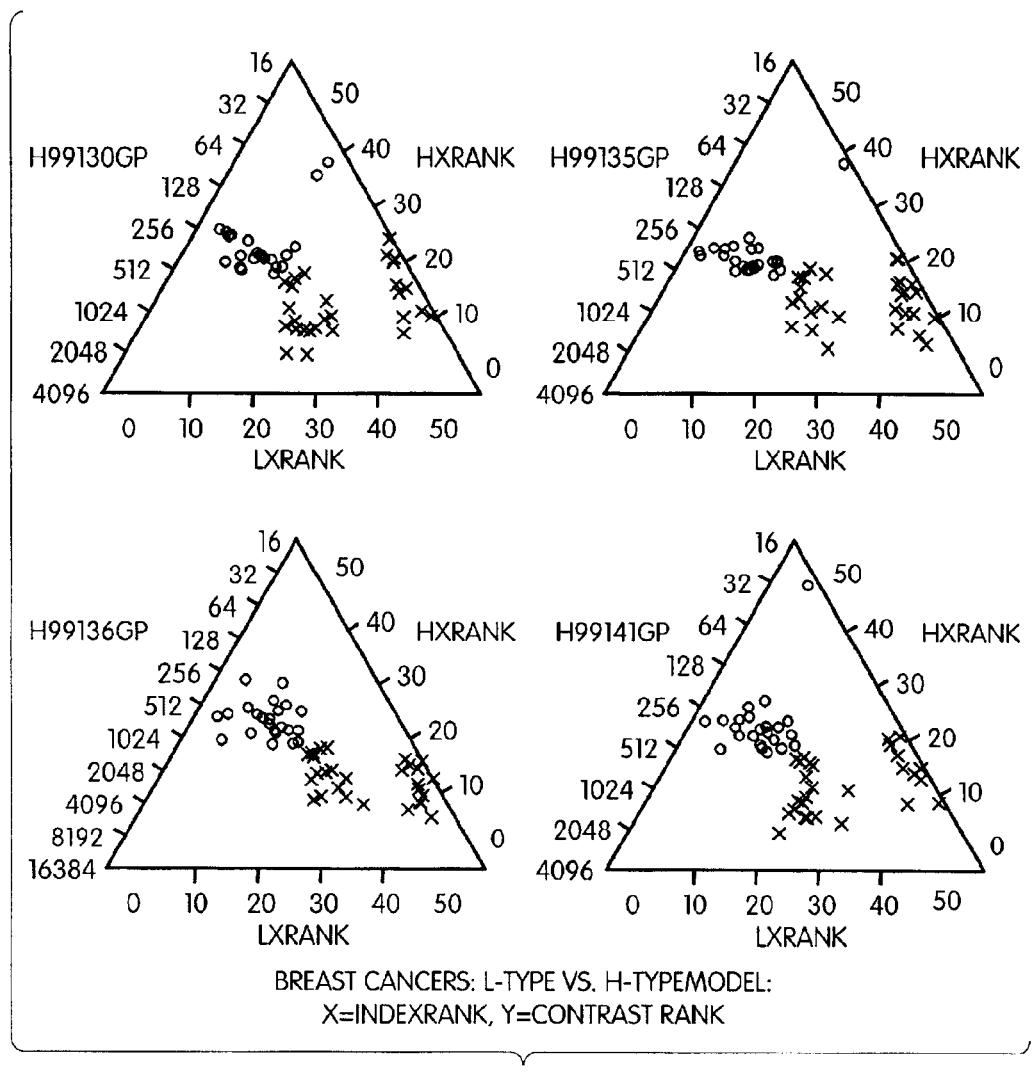

Another embodiment of the two-class model is based solely on the rank order of gene expression within the two compared training set groups. In this approach, a list of discriminating genes was selected as above from a training set using standard statistical approaches. Gene expression for each tissue class was rank ordered as above by abundance, and these two model elements (rank order of index tissue group, RANK-I; rank order of contrasting tissue group, RANK-C) were plotted against an unknown sample (log transformed). FIGS. 4–6 are examples plotted in this manner using a triangular, or ternary, coordinate system from the same datasets shown in FIGS. 1–3, respectively. The X (lower) axis shows rank ordered training set index tissue, Y (right) axis shows rank ordered training set contrasting tissue, and Z (left) axis shows unknown or challenge tissue. In particular, this model displays excellent graphic displacement of datapoints representing genes (cross symbols) expressed at a higher level in index (X axis) compared to contrasting (Y axis) training set tissues. Differences in these data presentations may be observed by comparing the shift of cross-symbol data clouds between FIGS. 1 and 4, 2 and 5, 3 and 6.

Data Processing Flowchart

1. Model defined by gene (a,b,c,d, . . . ) expression in Training Set of 2 tissue classes:
   Index and Contrasting tissues.
   Calculate expression mean and differences for expression of each gene a,b,c,d . . .
   $Im_{a,b,c} \ldots$ =Index group mean
   $Cm_{a,b,c} \ldots$ =Contrast group mean
   $Cm_{a,b,c} \ldots - Im_{a,b,c} \ldots = Dm_{a,b,c} \ldots$ =Difference of means 2. Convert 2-variable Model to (lowest-highest) rank order:
   $Ir_{a,b,c} \ldots = Im_{a,b,c} \ldots$ rank order
   $Cr_{a,b,c} \ldots = Cm_{a,b,c} \ldots$ rank order
   $Dr_{a,b,c} \ldots = Dm_{a,b,c} \ldots$ rank order 3. Symbols coded by positive/negative direction of Dm
   Dm<0, symbol=circle
   Dm>0, symbol=cross 4. Log transform unknown tissue to be plotted against model=U
   Log Transform U;

5. Each gene (a,b,c, . . . ) is plotted as one symbol, in three dimensions on a ternary (triangular) plot. Two dimensions define the model (X,Y), and one dimension (Z) is the challenge case.

| Coordinate | Gene a | Gene b | Gene c |
|---|---|---|---|
| X (lower) axis | $Ir_a$ | $Ir_b$ | $Ir_c$ |
| Y (right) axis | $Dr_a$ | $Dr_b$ | $Dr_c$ |
| Z (left) axis: | $\log2(U)_a$ | $\log2(U)_b$ | $\log2(U)_c$ |

6. Interpret Graphic Signature Created by Plotting Unknown against model Examples shown in FIGS. 1–3

Another Embodiment

Step 5 of the flowchart was modified as follows. The Rank order of the Contrasting tissue expression ($Cr_{a,b,c} \ldots = Cm_{a,b,c} \ldots$ rank order) is plotted on the Y axis. Thus:

| Coordinate | Gene a | Gene b | Gene c |
|---|---|---|---|
| X (lower) axis | $Ir_a$ | $Ir_b$ | $Ir_c$ |
| Y (right) axis | $Cr_a$ | $Cr_b$ | $Cr_c$ |
| Z (left) axis: | $\log2(U)_a$ | $\log2(U)_b$ | $\log2(U)_c$ |

Interpretation according to step 6 of the flowchart yields the exemplary graphs shown in FIGS. 4–6.

Each references cited herein is hereby incorporated by reference.

While the invention has been described with respect to certain embodiments, it should be appreciated that many modifications and changes may be made by those of ordinary skill in the art without departing from the spirit of the invention. It is intended that such modification, changes and equivalents fall within the scope of the following claims.

What is claimed is:

1. A method of classifying an unknown tissue, comprising steps of:

measuring values of each variable of a set of variables for an index group of tissues and a contrast group of tissues, calculating mean value and differences of mean value for each variable of the set of variables from the index group of tissues and the contrast group of tissues, ranking the means and differences of the means between the index and the contrast groups, determining values of each variable in the set of variables in an unknown tissue, and comparing the measured values in the unknown tissue to rank orders selected from the group consisting of ranked means of the index group, ranked means of the contrast group, and differences of the means between the index and the contrast groups to classify the unknown tissue.

2. The method according to claim 1, further comprising:

displaying to a user a visual indication of a relationship described by the comparison of the measured values of variables in the unknown tissue and the rank orders of the index and contrast groups.

3. The method according to claim 2, further comprising the step of coding symbols based on the positive or negative values of the means and the differences of the means.

4. The method according to claim 2, wherein the visual indication is a ternary plot.

5. The method according to claim 1, wherein the variables are genes and the values are levels of gene expression.

6. The method according to claim 5, wherein the values are expressed as log of gene expression.

* * * * *